United States Patent
Izumi et al.

(10) Patent No.: US 9,487,693 B2
(45) Date of Patent: Nov. 8, 2016

(54) CHROMENE COMPOUND

(75) Inventors: Shinobu Izumi, Shunan (JP); Kazuhiro Teranishi, Shunan (JP); Yusuke Daikoku, Shunan (JP); Mitsuyoshi Sando, Shunan (JP)

(73) Assignee: TOKUYAMA CORPORATION, Shunan-Shi, Yamaguchi (JP)

( * ) Notice: Subject to any disclaimer, the term of this patent is extended or adjusted under 35 U.S.C. 154(b) by 51 days.

(21) Appl. No.: 14/129,069

(22) PCT Filed: Jun. 19, 2012

(86) PCT No.: PCT/JP2012/066099
§ 371 (c)(1),
(2), (4) Date: Feb. 12, 2014

(87) PCT Pub. No.: WO2012/176918
PCT Pub. Date: Dec. 27, 2012

(65) Prior Publication Data
US 2014/0154527 A1 Jun. 5, 2014

(30) Foreign Application Priority Data

Jun. 23, 2011 (JP) ................................ 2011-139347

(51) Int. Cl.
| | | |
|---|---|---|
| C07C 21/22 | (2006.01) | |
| C09K 9/02 | (2006.01) | |
| C07C 39/17 | (2006.01) | |
| C07C 43/23 | (2006.01) | |
| G02B 5/23 | (2006.01) | |
| C07C 323/21 | (2006.01) | |
| C07C 39/23 | (2006.01) | |
| C07D 311/92 | (2006.01) | |
| C07D 327/04 | (2006.01) | |
| C07D 497/10 | (2006.01) | |

(Continued)

(52) U.S. Cl.
CPC ............... *C09K 9/02* (2013.01); *C07C 39/17* (2013.01); *C07C 39/23* (2013.01); *C07C 43/23* (2013.01); *C07C 323/21* (2013.01); *C07D 295/096* (2013.01); *C07D 311/92* (2013.01); *C07D 327/04* (2013.01); *C07D 497/10* (2013.01); *G02B 5/23* (2013.01); *C07C 2101/04* (2013.01); *C07C 2101/08* (2013.01); *C07C 2101/14* (2013.01); *C07C 2101/16* (2013.01); *C07C 2103/94* (2013.01); *C08L 83/04* (2013.01); *C09K 2211/1007* (2013.01); *C09K 2211/1011* (2013.01); *C09K 2211/1088* (2013.01); *Y10T 428/31504* (2015.04)

(58) Field of Classification Search
CPC .................................................. C07C 2103/22
See application file for complete search history.

(56) References Cited

U.S. PATENT DOCUMENTS 6,723,859 B2  4/2004  Kawabata et al.
8,529,789 B2  9/2013  Momoda et al.
(Continued)

FOREIGN PATENT DOCUMENTS

JP    2009-67680 A    4/2009
WO    WO 96/14596 A   5/1996
(Continued)

OTHER PUBLICATIONS

International Search Report issued in PCT/JP2012/066099 mailed Sep. 11, 2012.
(Continued)

*Primary Examiner* — Noble Jarrell
*Assistant Examiner* — John S Kenyon
(74) *Attorney, Agent, or Firm* — Birch, Stewart, Kolasch & Birch, LLP

(57) ABSTRACT

A chromene compound having a short fading half period, especially, a short fading half period even at a low temperature in a general-purpose polymer solid matrix. The chromene compound is represented by the following formula (1).

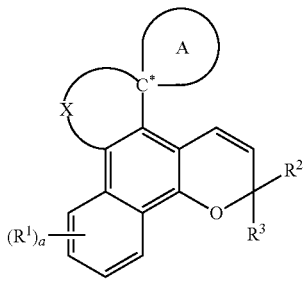

(1)

wherein $R^1$ is a hydroxyl group or the like, $R^2$ and $R^3$ are each an aryl group or the like, $C^*$ is a spiro carbon atom, a spiro ring A represented by the following formula is a saturated hydrocarbon ring having 4 to 12 ring member carbon atoms or the like, and at least one ring member carbon atom constituting the ring A is a group represented by the following formula (4), and X is a divalent group such as arylene group,

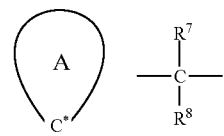

(4)

wherein $R^7$ and $R^8$ are each a cycloalkyl group or the like.

5 Claims, 1 Drawing Sheet

(51) Int. Cl.
*C07D 295/096* (2006.01)
*C08L 83/04* (2006.01)

(56) References Cited

U.S. PATENT DOCUMENTS

| | | |
|---|---|---|
| 2003/0096117 A1 | 5/2003 | Kawabata et al. |
| 2004/0014995 A1 | 1/2004 | Kawabata et al. |
| 2005/0263745 A1 | 12/2005 | Momoda et al. |
| 2005/0269556 A1 | 12/2005 | Evans et al. |
| 2008/0006798 A1 | 1/2008 | Evans et al. |
| 2010/0230650 A1 | 9/2010 | Nagoh et al. |
| 2012/0121934 A1 | 5/2012 | Takahashi et al. |
| 2012/0228567 A1 | 9/2012 | Izumi et al. |

FOREIGN PATENT DOCUMENTS

| | | |
|---|---|---|
| WO | WO 01/05854 A1 | 1/2001 |
| WO | WO 01/60811 A1 | 8/2001 |
| WO | WO 2004/041961 A1 | 5/2004 |
| WO | WO 2011/016582 A1 | 2/2011 |
| WO | WO 2011/059117 A1 | 5/2011 |

OTHER PUBLICATIONS

Clive et al., "Formal Radical Cyclization onto Benzene Rings: A General Method and its Use in the Synthesis of ent-Nocardione A," J. Org. Chem., vol. 69, 2004, pp. 3282-3293.

Gourdoupis, "A Direct and Versatile Synthesis of 5-(2-Di-n-Propylamino-Ethyl)-7-Methoxyindole," Synthetic Communications, vol. 23, No. 16, 1993, pp. 2241-2249.

International Preliminary Report on Patentability and Translation of the Written Opinion of the International Searching Authority (Forms PCT/IB/338, PCT/IB/373 and PCT/ISA/237), dated Jan. 9, 2014 for International Application No. PCT/JP2012/066099.

Chinese Office Action dated Dec. 12, 2014, issued in corresponding Chinese Patent Application No. 201280022587.5.

Extended European Search Report dated Nov. 12, 2014, issued in corresponding European Patent Application No. 12803316.4.

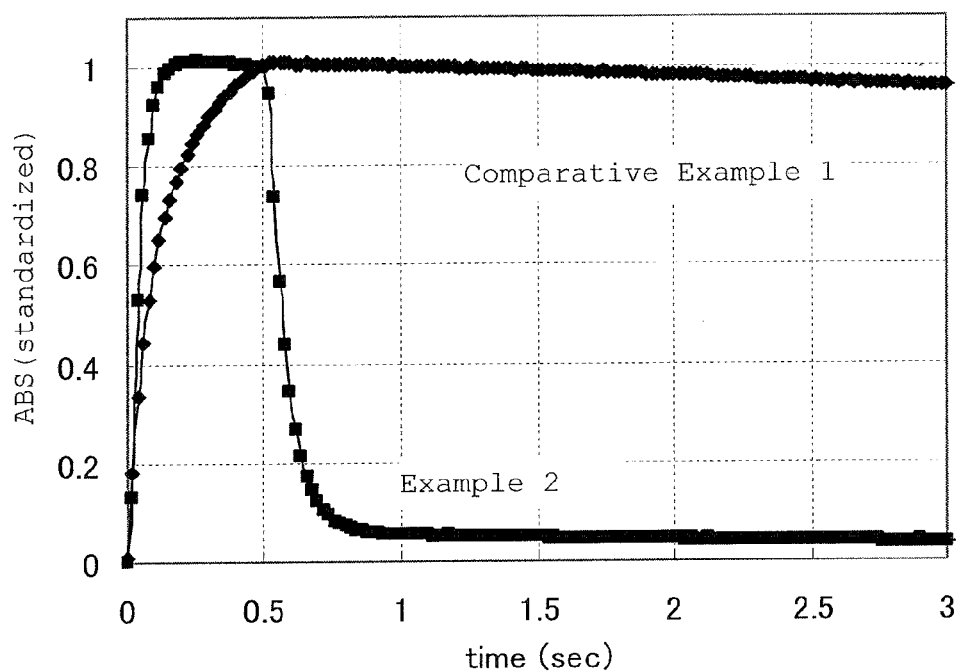

CHROMENE COMPOUND

TECHNICAL FIELD

The present invention relates to a novel chromene compound and the use of the chromene compound.

BACKGROUND ART

Photochromism is the reversible function of a certain compound that it changes its color upon exposure to light including ultraviolet light such as sunlight or light from a mercury lamp (color development) and returns to its original color when it is put in the dark by stopping its exposure to light (fading). A compound having this property is called "photochromic compound". One of the uses of the photochromic compound is a light control material for sunglasses, and chromene compounds, spirooxazine compounds and spiropyran compounds have been used as the photochromic compound.

Since the chromene compounds in particular have excellent light resistance and obtain various developed colors by optimizing a substituent, a large number of studies have been made. For example, there is known a chromene compound having an indeno(2,1-f)naphtho(1,2-b)pyran structure represented by the following formula (1) (refer to International Laid-Open WO1996/14596).

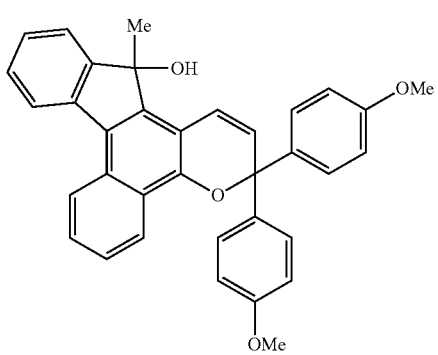

(I)

In the above formula, Me is a methyl group. The same shall apply to the formulas below.

Also, there is known a compound represented by the following formula (II) as a chromene compound having a short fading half period (International Laid-open WO2001/60811).

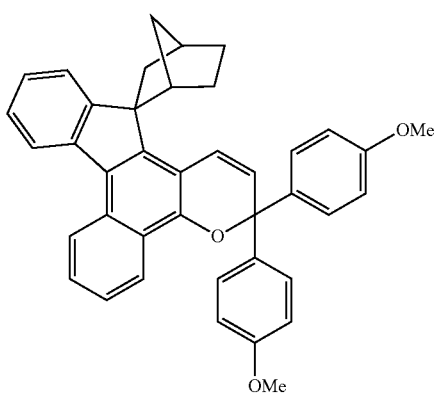

(II)

Since this chromene compound has a spiro ring bonded to the 13-position carbon atom, it has a short fading half period due to this structure.

However, even the above chromene compounds have room for the improvement of environmental dependence and temperature dependence. A description is first given of environmental dependence.

(Environmental Dependence)

The color of the chromene compound is changed by its structural change. Therefore, the chromene compound has quick optical response in an environment in which the structural change readily occurs as in a solution. However, in an environment in which the structural change hardly occurs as in a polymer solid matrix, the optical response is slow and the fading half period tends to be prolonged, that is, the optical response tends to deteriorate. This reason is considered to be that the structural change of the chromene compound is restricted due to a very small free space in the polymer solid matrix as compared with that in the solution. This problem tends to become marked particularly when the chromene compound is kneaded into a synthetic resin (polymer) having high hardness or high heat resistance.

To improve this, a method for improving the polymer solid matrix is proposed. For example, there is known a method in which a chromene compound is dispersed into a polymer solid matrix by using a curable composition comprising a monomer from which a resin having high hardness is obtained, a monomer from which a resin having low hardness is obtained and a photochromic compound (International Laid-open WO2001/005854). Also, there is known a method in which a chromene compound is dispersed into a polymer solid matrix by bonding a polysiloxane oligomer to a photochromic compound (International Laid-open WO2004/041961). Further, there is known a method in which a chromene compound is dispersed into a polymer solid matrix by using a curable composition comprising a monomer from which a resin having high hardness is obtained, a monomer from which a resin having low hardness is obtained and a photochromic compound (International Laid-open WO2001/005854).

According to these methods, even when a conventional chromene compound is used, the fading half period can be shortened to a certain extent as compared with other polymer solid matrices. However, since these methods do not aim to shorten the fading half period of the chromene compound itself, there is limitation to the improvement of the fading half period. Therefore, to further improve the optical response of a chromene compound in a polymer solid matrix, that is, to shorten the fading half period, the chromene compound itself must be improved.

(Temperature Dependence)

The chromene compound is a T type photochromic compound which returns to an achromatic state by heat. It is known that the fading half period of this photochromic compound greatly depends on temperature and becomes long at a low temperature.

For example, when the chromene compound represented by the above formula (II) is dispersed into a certain polymer solid matrix, the fading half period of the chromene compound is 50 seconds at 23° C. and 300 seconds at 10° C. Although it is known that conventional chromene compounds have a very long fading half period at a low temperature, requirements for the chromene compounds are becoming higher and the development of a compound having a short fading half period even at a low temperature has been desired.

To improve the above-described environmental dependence and temperature dependence, a chromene compound having optical response which is several times faster, that is, a fading half period which is several times shorter than that of a conventional chromene compound is needed. However, there has been unknown such a chromene compound. Since it is considered that a chromene compound which has quick optical response, that is, a short half period at a low temperature in a general-purpose polymer solid matrix, can be used for various purposes, the development of such a chromene compound has been desired.

DISCLOSURE OF THE INVENTION

It is therefore an object of the present invention to provide a chromene compound having remarkably improved optical response, especially excellent optical response even at a low temperature (short fading half period).

The inventors of the present invention conducted intensive studies to attain the above object. As a result, they found that a compound having a specific substituent introduced into a spiro ring in a naphtho(1,2-b)pyran structure containing spiro carbon exhibits an extremely short fading half period. The present invention was accomplished based on this finding.

That is, the present invention is a chromene compound represented by the following formula (1).

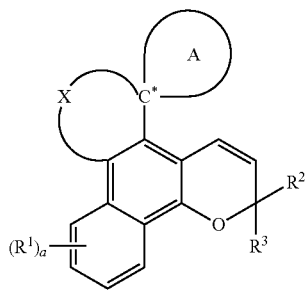

(1)

In the above formula, $R^1$ is a hydroxyl group, alkyl group, haloalkyl group, cycloalkyl group, alkoxy group, amino group, heterocyclic group having a ring member nitrogen atom and bonded to a benzene ring to which the heterocyclic group bonded via the nitrogen atom, cyano group, nitro group, formyl group, hydroxycarbonyl group, alkylcarbonyl group, alkoxycarbonyl group, halogen atom, aralkyl group, aralkoxy group, aryloxy group, aryl group, heteroaryl group, alkylthio group, cycloalkylthio group, arylthio group, heteroarylthio group or group having a siloxane bond.

"a" is an integer of 0 to 4. When "a" is 2 to 4, a plurality of $R^1$'s may be the same or different, and two $R^1$'s may be bonded together to form a ring.

$R^2$ and $R^3$ are each an alkyl group, aryl group, heteroaryl group, group represented by the following formula (2), or group represented by the following formula (3).

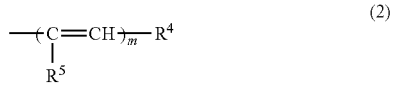

(2)

In the above formula, $R^4$ is an aryl group or heteroaryl group, $R^5$ is a hydrogen atom, alkyl group or halogen atom, and "m" is an integer of 1 to 3.

(3)

In the above formula, $R^6$ is an aryl group or heteroaryl group, and "n" is an integer of 1 to 3.

$R^2$ and $R^3$ may form an aliphatic ring together with carbon atoms bonded thereto.

C* is a spiro carbon atom, a spiro ring A represented by the following formula is a saturated hydrocarbon ring or unsaturated hydrocarbon ring having 4 to 12 carbon atoms constituting the ring, and at least one ring member carbon atom constituting the spiro ring A is a group represented by the following formula (4).

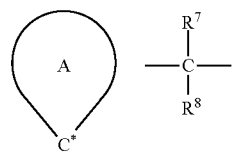

(4)

In the above formula, $R^7$ and $R^8$ are each an alkyl group having 3 or more carbon atoms, aralkyl group, cycloalkyl group, aryl group or heteroaryl group.

X is a divalent group selected from alkylene group, alkynylene group, cycloalkylene group, arylene group and alkylene-arylene group.

The second invention is a photochromic curable composition which comprises the chromene compound of the present invention and a polymerizable monomer.

The third invention is a photochromic optical article having a polymer molded product containing the chromene compound of the present invention dispersed therein as a constituent member. In the fourth place, the present invention is an optical article having an optical substrate all or part of at least one surface of which is coated with a polymer film comprising the chromene compound of the present invention dispersed therein as a constituent member.

The fourth invention is a naphthol compound represented by the formula (4) which will be described hereinafter and a raw material of the chromene compound represented by the above formula (1).

BRIEF DESCRIPTION OF THE DRAWINGS

FIG. 1 is a graph showing time changes in the optical color density of each of the chromene compound (E1) of Example 2 and the chromene compound (CE1) of Comparative Example 1.

BEST MODE FOR CARRYING OUT THE INVENTION

The chromene compound of the present invention is a compound having a naphtho(1,2-b)pyran structure represented by the following formula (1).

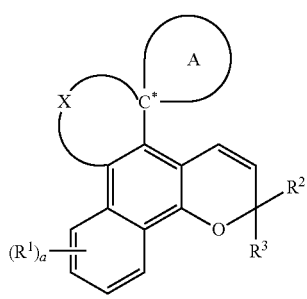

(1)

The chromene compound of the present invention has a big feature in terms of chemical structure that it has a spiro ring A bonded to a spiro carbon atom C* and at least one ring member carbon atom constituting the spiro ring is substituted by the same or two different groups selected from alkyl groups having 3 or more carbon atoms, aralkyl groups, cycloalkyl groups, aryl groups and heteroaryl groups.

It has been known that the fading half period of a chromene compound, for example, a compound having an indeno(2,1-f)naphtho(1,2-b)pyran structure is shortened according to the type of a spiro ring group. However, it has been unknown that the fading half period of a chromene compound into which a spiro ring containing a ring member carbon atom having specific substituents like above as a constituent component has been introduced becomes remarkably short. It has also been unknown that the fading half period of the above chromene compound is very short even at a low temperature.

A detailed description is subsequently given of the chromene compound of the present invention.

<Substituent $R^1$>

$R^1$ is a hydroxyl group, alkyl group, haloalkyl group, cycloalkyl group, alkoxy group, amino group, heterocyclic group containing a ring member nitrogen atom and bonded to a benzene ring (more specifically, the carbon atom of a benzene ring) bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group, aryl group, heteroaryl group, alkylthio group, cycloalkylthio group, arylthio group, heteroarylthio group or group having a siloxane bond.

The above alkyl group is preferably an alkyl group having 1 to 6 carbon atoms. Preferred examples of the alkyl group include methyl group, ethyl group, n-propyl group, isopropyl group, n-butyl group, sec-butyl group, tert-butyl group, pentyl group and hexyl group.

The above haloalkyl group is preferably an alkyl group having 1 to 6 carbon atoms and substituted by a fluorine atom, chlorine atom or bromine atom. Preferred examples of the haloalkyl group include trifluoromethyl group, tetrafluoroethyl group, chloromethyl group, 2-chloroethyl group and bromomethyl group.

The above cycloalkyl group is preferably a cycloalkyl group having 3 to 8 carbon atoms. Preferred examples of the cycloalkyl group include cyclopropyl group, cyclobutyl group, cyclopentyl group and cyclohexyl group.

The above alkoxy group is preferably an alkoxy group having 1 to 6 carbon atoms. Preferred examples of the alkoxy group include methoxy group, ethoxy group, n-propoxy group, isopropoxy group, n-butoxy group, sec-butoxy group and tert-butoxy group.

The above amino group is not limited to a primary amino group ($-NH_2$) and may be a secondary or tertiary amino group whose one or two hydrogen atoms are substituted. Examples of the substituent of the amino group include alkyl groups having 1 to 6 carbon atoms, haloalkyl groups having 1 to 6 carbon atoms, alkoxy groups having 1 to 6 carbon atoms, cycloalkyl groups having 3 to 7 carbon atoms, aryl groups having 6 to 14 carbon atoms and heteroaryl groups having 4 to 14 carbon atoms. Preferred examples of the amino group include amino group, methylamino group, dimethylamino group, ethylamino group, diethylamino group, phenylamino group and diphenylamino group.

Preferred examples of the above heterocyclic group containing a ring member nitrogen atom and bonded to a benzene ring bonded thereto via the nitrogen atom include aliphatic heterocyclic groups such as morpholino group, piperidino group, pyrrolidinyl group, piperazino group and N-methylpiperazino group, and aromatic heterocyclic groups such as indolinyl group. Further, the heterocyclic group may have a substituent. A preferred example of the substituent is an alkyl group. Preferred examples of the heterocyclic group having a substituent include 2,6-dimethylmorpholino group, 2,6-dimethylpiperidino group and 2,2,6,6-tetramethylpiperidino group.

The above alkylcarbonyl group is preferably an alkylcarbonyl group having 2 to 7 carbon atoms. Preferred examples of the alkylcarbonyl group include acetyl group and ethylcarbonyl group.

The above alkoxycarbonyl group is preferably an alkoxycarbonyl group having 2 to 7 carbon atoms. Preferred examples of the alkoxycarbonyl group include methoxycarbonyl group and ethoxycarbonyl group.

Examples of the above halogen atom are fluorine atom, chlorine atom, bromine atom and iodine atom.

The above aralkyl group is preferably an aralkyl group having 7 to 11 carbon atoms. Preferred examples of the aralkyl group include benzyl group, phenylethyl group, phenylpropyl group, phenylbutyl group and naphthylmethyl group.

The above aralkoxy group is preferably an aralkoxy group having 7 to 11 carbon atoms. Preferred examples of the aralkoxy group include benzyloxy group and naphthylmethoxy group.

The above aryloxy group is preferably an aryloxy group having 6 to 12, carbon atoms. Preferred examples of the aryloxy group include phenyloxy group and naphthyloxy group.

The above aryl group is preferably an aryl group having 6 to 14 carbon atoms. Preferred examples of the aryl group include phenyl group, 1-naphthyl group and 2-naphthyl group.

1 to 7 hydrogen atoms, particularly preferably 1 to 4 hydrogen atoms of the aromatic ring of each of the aralkyl group, the aralkoxy group, the aryloxy group and the aryl group may be substituted by the above hydroxyl group, alkyl group, haloalkyl group, cycloalkyl group, alkoxy group, amino group, heterocyclic group having a ring member nitrogen atom and bonded to an aromatic ring bonded thereto via the nitrogen atom, cyano group, nitro group or halogen atom.

The above heteroaryl group is not particularly limited but preferably a heteroaryl group comprising an aromatic ring having 5 to 7 ring members including 1 to 2 oxygen atoms, nitrogen atoms or sulfur atoms or a condensed ring of the aromatic ring and a benzene ring. The heteroaryl group is bonded to a benzene ring bonded thereto via a carbon atom and not a hetero atom. Preferred examples of the heteroaryl group include thienyl group, furyl group, pyrrolinyl group, pyridyl group, benzothienyl group, benzofuranyl group and benzopyrrolinyl group. 1 to 6 hydrogen atoms, particularly preferably 1 to 4 hydrogen atoms of the aromatic ring of the heteroaryl group may be substituted by the above hydroxyl group, alkyl group, haloalkyl group, cycloalkyl group, alkoxy group, amino group, heterocyclic group having a ring member nitrogen atom and bonded to an aromatic group bonded thereto via the nitrogen atom, cyano group, nitro group or halogen atom.

The above alkylthio group is preferably an alkylthio group having 1 to 6 carbon atoms. Preferred examples of the alkylthio group include methylthio group, ethylthio group, n-propylthio group, isopropylthio group, n-butylthio group, sec-butylthio group and tert-butylthio group.

The above cycloalkylthio group is preferably a cycloalkylthio group having 3 to 8 carbon atoms. Preferred examples of the cycloalkylthio group include cyclopropylthio group, cyclobutylthio group, cyclopentylthio group and cyclohexylthio group.

The above arylthio group is preferably an arylthio group having 6 to 10 carbon atoms. Preferred examples of the arylthio group include phenylthio group, 1-naphthylthio group and 2-naphthylthio group.

The above heteroarylthio group is preferably a heteroarylthio group having 4 to 12 carbon atoms. Preferred examples of the heteroarylthio group include thienylthio group, furylthio group, pyrrolylthio group, pyridylthio group, benzothienylthio group, benzofurylthio group and benzopyrrolylthio group.

1 to 5 hydrogen atoms, particularly preferably 1 to 4 hydrogen atoms of the aromatic ring of each of the above arylthio group and the above heteroarylthio group may be substituted by an alkyl group having 1 to 6 carbon atoms, alkoxy group having 1 to 6 carbon atoms, cycloalkyl group having 3 to 8 carbon atoms, or halogen atom.

The above group having a siloxane bond is preferably a group represented by the following formula (G).

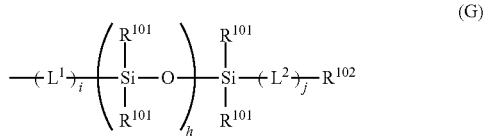

(G)

In the above formula, $R^{101}$'s are each independently an alkyl group or aryl group, $R^{102}$ is a hydrogen atom, hydroxyl group, hydroxycarbonyl group, alkyl group, haloalkyl group, alkylcarbonyl group, alkoxycarbonyl group, acryloyl group, methacryloyl group or vinyl group, $L^1$ and $L^2$ are each independently a divalent group, "h" is an integer of 2 to 100, "i" is an integer of 1 to 10, and "j" is an integer of 1 to 10.

In the above formula (G), the alkyl group, the aryl group, the alkylcarbonyl group, the alkoxycarbonyl group and the haloalkyl group are the same as those explained above.

In the above formula (G), $L^1$ and $L^2$ are each a divalent group selected from alkylene group having 1 to 20 carbon atoms, phenylene group, oxygen atom (—O—), sulfur atom (—S—) and carbonyl group (—C(=O)—).

"h" is an integer of 2 to 100 indicative of the number of siloxane units in the above formula (G).

"i" and "j" are each an integer of 1 to 10 indicative of the numbers of divalent groups $L^1$'s and $L^2$'s, respectively.

When "i" or "j" is an integer of 2 to 10, a plurality of $L^1$'s or a plurality of $L^2$'s may be the same or different.

"a" is an integer of 0 to 4 indicative of the number of $R^1$'s. When "a" is an integer of 2 to 4, a plurality of $R^1$'s may be the same or different.

When two $R^1$'s are existent at adjacent carbon atoms, they may form a ring together with the carbon atoms bonded thereto. The number of atoms constituting the ring is preferably 4 to 8, particularly preferably 5 or 6. This ring may be an aliphatic ring or a hetero ring containing an oxygen atom or a nitrogen atom. This ring may have a substituent. In the case of a hetero ring having a nitrogen atom, the nitrogen atom may have a substituent. Preferred examples of the substituent of the ring include alkyl groups, haloalkyl groups and halogen atoms.

The above-described $R^1$ has a great influence upon the developed color of the obtained chromene compound according to the number of the groups and the bonding position and can be suitably selected to obtain a desired color.

<Substituents $R^2$ and $R^3$>

$R^2$ and $R^3$ are each an alkyl group, aryl group, heteroaryl group, group represented by the following formula (2) or group represented by the following formula (3).

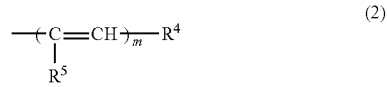

The above alkyl group, aryl group and heteroaryl group are the same as those explained for $R^1$.

$R^4$ in the above formula (2) is an aryl group or heteroaryl group. $R^5$ is a hydrogen atom, alkyl group or halogen atom. These groups are the same as those explained for $R^1$.

"m" is an integer of 1 to 3. It is preferably 1 from the viewpoint of the acquisition ease of raw materials.

Preferred examples of the group represented by the above formula (2) include phenyl-ethenyl group, (4-(N,N-dimethylamino)phenyl)-ethenyl group, (4-morpholinophenyl)-ethenyl group, (4-piperidinophenyl)-ethenyl group, (4-methoxyphenyl)-ethenyl group, (2-methoxyphenyl)-ethenyl group, phenyl-1-methylethenyl group, (4-methoxyphenyl)-1-methylethenyl group, phenyl-1-fluoroethenyl group, (4-(N,N,-dimethylamino)phenyl)-1-fluoroethenyl group, 2-thienyl-ethenyl group, 2-furyl-ethenyl group, 2-(N-methyl)pyrrolinyl-ethenyl group, 2-benzothienyl-ethenyl group, 2-benzofuranyl-ethenyl group and 2-(N-methyl)indolyl-ethenyl group.

In the above formula (3), $R^6$ is an aryl group or heteroaryl group. It is understood that these groups are the same as those explained for $R^4$. "n" is an integer of 1 to 3. From the viewpoint of the acquisition ease of raw materials, "n" is preferably 1.

Preferred examples of the group represented by the above formula (3) include phenyl-ethynyl group, (4-(N,N-dimethylamino)phenyl)-ethynyl group, (4-morpholinophenyl)-ethynyl group, (4-piperidinophenyl)-ethynyl group, (4-methoxyphenyl)-ethynyl group, (4-methylphenyl)-ethynyl group, (2-methoxyphenyl)-ethynyl group, 2-thienyl-ethynyl group, 2-furyl-ethynyl group, 2-(N-methyl)pyrrolinyl-ethynyl group, 2-benzothienyl-ethynyl group, 2-benzofuranyl-ethynyl group and 2-(N-methyl)indolyl-ethynyl group.

$R^2$ and $R^3$ may form an aliphatic hydrocarbon ring together with the carbon atom bonded thereto. Preferred examples of the aliphatic hydrocarbon ring include adamantane ring, bicyclononane ring, norbornane ring and fluorene ring.

In order for the chromene compound of the above formula (1) to exhibit particularly excellent photochromic properties (optical color density and durability), at least one, preferably both of $R^2$ and $R^3$ are each an aryl group or heteroaryl group, particularly preferably an aryl group having at least one substituent selected from alkyl group, alkoxy group, group having a siloxane bond, amino group and heterocyclic group having a ring member nitrogen atom and bonded to an aromatic ring bonded thereto via the nitrogen atom. The one substituent is particularly preferably existent at the para-position. Preferred examples of the aryl group include 4-methylphenyl group, 4-methoxyphenyl group, 3,4-dimethoxyphenyl group, 4-n-propoxyphenyl group, 4-(N,N-dimethylamino) phenyl group, 4-(N,N-diethylamino)phenyl group, 4-morpholinophenyl group, 4-piperidinophenyl group, 3-(N,N-dimethylamino)phenyl group and 4-(2,6-dimethylmorpholino)phenyl group.

<Spiro Ring A>

In the above formula (1), C* is a spiro carbon atom. The spiro ring A containing C* is a saturated hydrocarbon ring or unsaturated hydrocarbon ring having 4 to 12 carbon atoms. At least one ring member carbon atom constituting the spiro ring A must be a group represented by the following formula (4).

(4)

In the above formula, $R^7$ and $R^8$ are each an alkyl group having 3 or more carbon atoms, aralkyl group, cycloalkyl group, aryl group or heteroaryl group.

The above alkyl group having 3 or more carbon atoms is preferably an alkyl group having 3 to 10 carbon atoms and more preferably a branched alkyl group. Preferred examples of the alkyl group having 3 or more carbon atoms include isopropyl group, tert-butyl group, isobutyl group and isopentyl group.

The above aralkyl group is preferably an aralkyl group having 7 to 11 carbon atoms. Preferred examples of the aralkyl group include benzyl group, phenylethyl group, phenylpropyl group, phenylbutyl group and naphthylmethyl group.

The above cycloalkyl group is preferably a cycloalkyl group having 3 to 8 carbon atoms. Preferred examples of the cycloalkyl group include cyclopropyl group, cyclobutyl group, cyclopentyl group and cyclohexyl group.

The above aryl group is preferably an aryl group having 6 to 14 carbon atoms. Preferred examples of the aryl group include phenyl group, 1-naphthyl group and 2-naphthyl group.

The above heteroaryl group is not particularly limited but preferably a heteroaryl group comprising an aromatic ring having 5 to 7 ring members including 1 to 2 oxygen atoms, nitrogen atoms or sulfur atoms or a condensed ring of the aromatic ring and a benzene ring. The heteroaryl group is bonded to a carbon atom bonded thereto via a carbon atom and not a hetero atom. Preferred examples of the heteroaryl group include thienyl group, furyl group, pyrrolinyl group, pyridyl group, benzothienyl group, benzofuranyl group and benzopyrrolinyl group.

1 to 4 hydrogen atoms, particularly preferably 1 to 2 hydrogen atoms of each of the above cycloalkyl group, aryl group and heteroaryl group may be substituted. The substituents substituting the hydrogen atoms are preferably selected from the alkyl group, haloalkyl group, cycloalkyl group, alkoxy group, amino group, heterocyclic group containing a ring member nitrogen atom and bonded to a carbon atom bonded thereto via the nitrogen atom, and halogen atom all of which have been explained for the substituent $R^1$.

$R^7$ and $R^8$ may be the same or different. In consideration of the productivity and synthesis ease of the chromene compound, $R^7$ and $R^8$ are preferably the same.

The spiro ring A is a saturated hydrocarbon ring or unsaturated hydrocarbon ring having 4 to 12 carbon atoms forming the ring, that is, ring member carbon atoms. From the viewpoint of easily obtaining the effect of shortening the fading half period, the number of ring member carbon atoms is preferably 4 to 8, particularly preferably 4 to 6. At least one of the ring member carbon atoms is a group represented by the above formula (4) and the other ring member carbon atoms are methylene groups represented by the following formula or vinylene groups represented by the following formula.

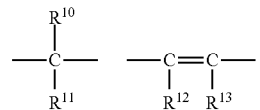

In the above formulas, $R^{10}$ to $R^{13}$ are each a hydrogen atom, hydroxyl group, alkyl group, haloalkyl group, alkoxy group or halogen atom. These substituents are the same as those enumerated for $R^1$. Out of these, the alkyl group, haloalkyl group and alkoxy group preferably have 1 to 5 carbon atoms.

<Preferred Spiro Ring A>

The spiro ring A has a bisubstituted methylene group represented by the above formula (4). A chromene compound having a very short fading half period is obtained due to the bulkiness of the substituent. Preferred examples of the spiro ring A are represented by the following formulas.

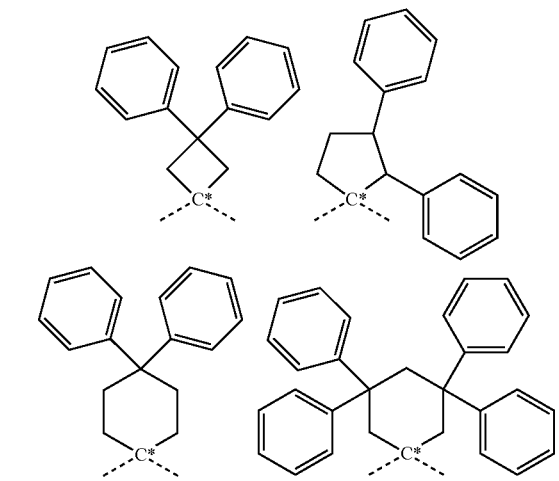

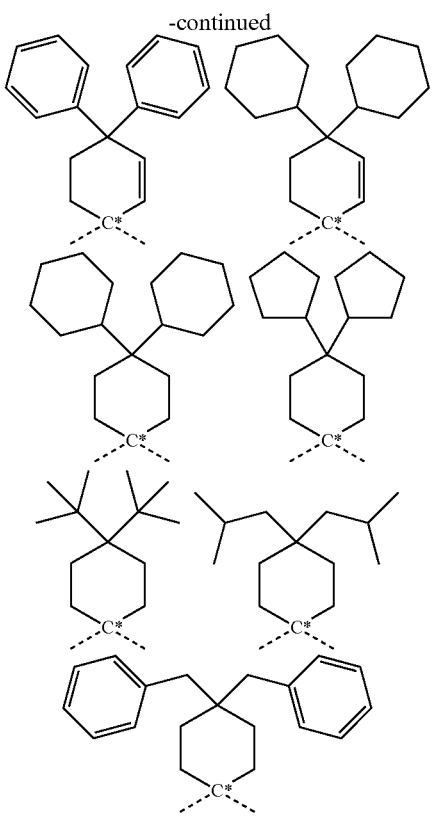

The carbon atom denoted by C* is the spiro carbon atom of the ring A.

<Divalent Group Represented by X>

In the above formula (1), X is a divalent group selected from alkylene group, alkynylene group, cycloalkylene group and arylene group, or a divalent group formed by bonding together an alkylene group and an arylene group.

The above alkylene group is an alkylene group having preferably 1 to 6 carbon atoms, particularly preferably 2 to 4 carbon atoms. Examples of the alkylene group include ethylene group, trimethylene group and tetramethylene group. At least one hydrogen atom of the alkylene group may be substituted. The substituent is an alkyl group having 1 to 6 carbon atoms.

The above alkynylene group is an alkynylene group having preferably 2 to 6 carbon atoms, particularly preferably 2 to 4 carbon atoms. Preferred examples of the alkynylene group include vinylene group, propenylene group, 1-butenylene group and 2-butenylene group. At least one hydrogen atom of the alkynylene group may be substituted by an alkyl group having 1 to 6 carbon atoms. In an alkynylene group having an asymmetrical structure, the bonding directions of the both ends of the alkynylene group are not particularly limited.

The above cycloalkylene group is a cycloalkylene group having preferably 5 to 10 carbon atoms, particularly preferably 5 to 8 carbon atoms. Preferred examples of the cycloalkylene group include cyclopentylene group, cyclohexylene group, cycloheptylene group and cyclooctylene group. At least one hydrogen atom of the cycloalkylene group may be substituted by an alkyl group having 1 to 6 carbon atoms.

The above arylene group is preferably an arylene group having 6 to 14 carbon atoms. Preferred examples of the arylene group include 1,2-phenylene group, 1,2-naphthylene group, 1,8-naphthylene group and 1,1-biphenylene group. At least one hydrogen atom of the arylene group may be substituted by a hydroxyl group, alkyl group, haloalkyl group, cycloalkyl group, alkoxy group, amino group, heterocyclic group containing a ring member nitrogen atom and bonded to a benzene ring bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group, aryl group, heteroaryl group, alkylthio group, cycloalkylthio group, arylthio group or heterarylthio group. These substituents are the same as those enumerated for $R^1$.

When the arylene group has a plurality of substituents, the substituents may be the same or different. Further, when the arylene group has a plurality of substituents, the substituents may form a ring together with the carbon atoms of the arylene group to which the substituents are bonded.

The alkylene-arylene group is a divalent group formed by bonding together an alkylene group and an arylene group, the alkylene group is preferably a methylene group, and the arylene group is preferably a phenylene group. The group formed by bonding together the methylene group and the phenylene group is preferably represented by the following formula.

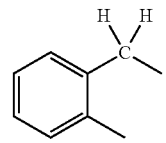

At least one hydrogen atom of the alkylene group or at least one hydrogen atom of the arylene group may be substituted. Examples of the substituent are the same as those enumerated for the above arylene group.

Since the chromene compound obtained by the present invention has high durability, the divalent group represented by X is preferably an arylene group, particularly preferably a 1,2-phenylene group. This 1,2-phenylene group may have a substituent.

<Preferred Chromene Compound>

As described above, the chromene compound of the present invention is such that X is preferably an arylene group. Stated more specifically, it is represented by the following formula (5).

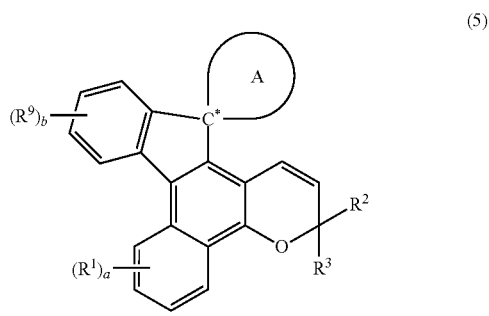

(5)

In the above formula, $R^1$, $R^2$, $R^3$, C*, spiro ring A and "a" are as defined in the above formula (1), $R^9$ is a hydroxyl group, alkyl group, haloalkyl group, cycloalkyl group, alkoxy group, amino group, heterocyclic group containing a ring member nitrogen atom and bonded to a benzene ring bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group, aryl group, heteroaryl group, alkylthio group, cycloalkylthio group, arylthio group or heteroarylthio group, "b" is an integer of 0 to 4, when "b" is 2 to 4, a plurality of $R^9$'s may be the same or different, and two $R^9$'s may be bonded together to form a ring.

The above alkyl group, haloalkyl group, cycloalkyl group, alkoxy group, amino group, heterocyclic group containing a ring member nitrogen atom and bonded to a benzene ring bonded thereto via the nitrogen atom, alkylcarbonyl group, alkoxycarbonyl group, halogen atom, aralkyl group, aralkoxy group, aryloxy group, aryl group, heteroaryl group, alkylthio group, cycloalkylthio group, arylthio group and heteroarylthio group represented by $R^9$ are the same as those explained for $R^1$.

"b" indicates the number of $R^9$'s, and when "b" is 2 or more, a plurality of $R^9$'s may be the same or different.

When two $R^9$'s are existent at adjacent carbon atoms, they may form a ring together with the carbon atoms bonded thereto. Examples of the ring are the same as those explained for $R^1$.

Further, particularly preferred examples of the chromene compound represented by the above formulas (5) are as follows.

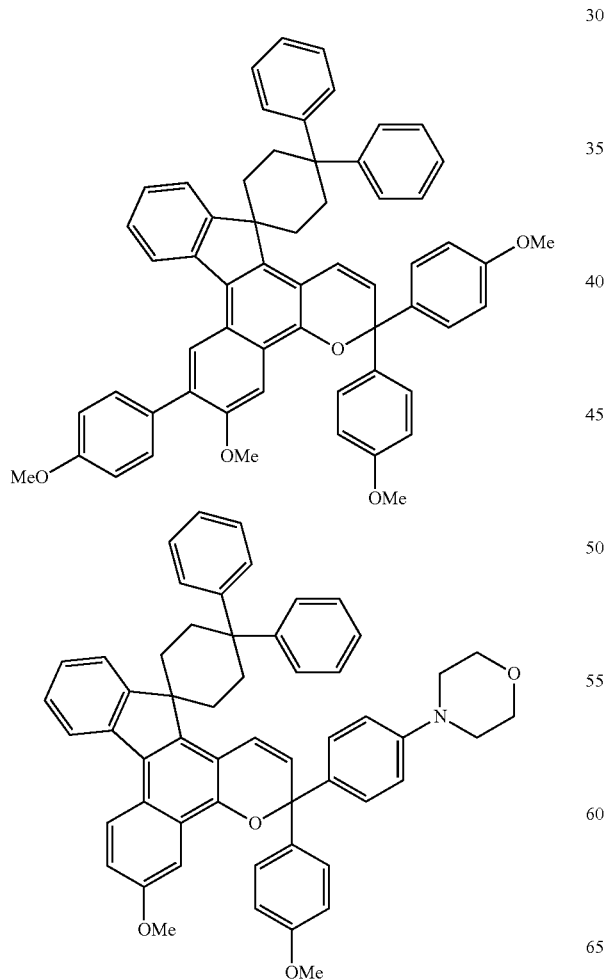

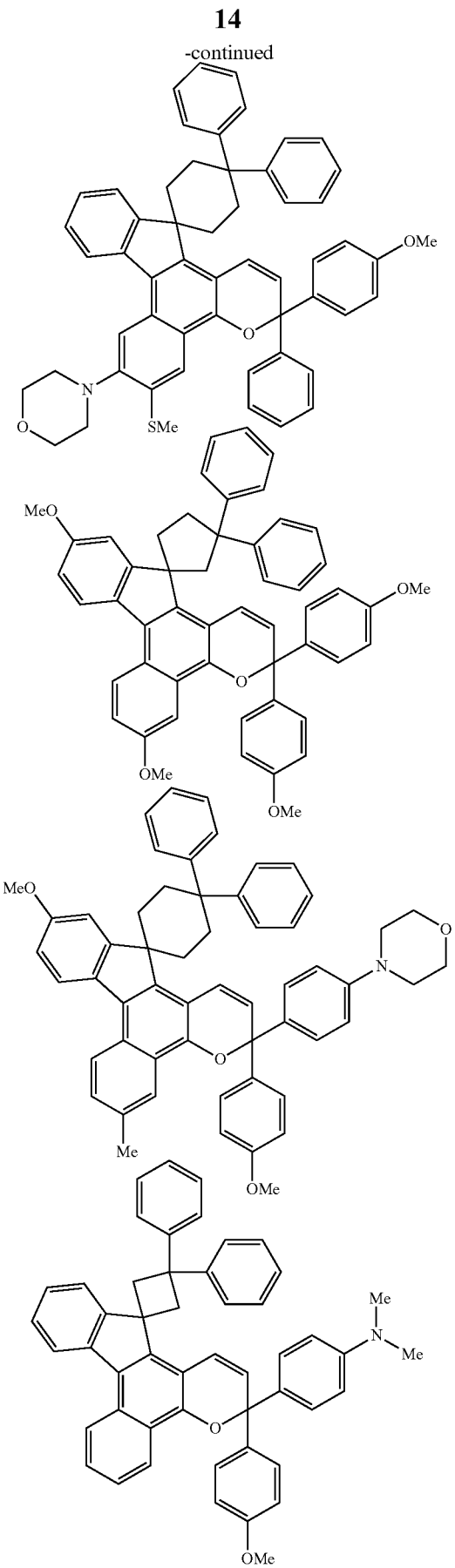

(Identification of Chromene Compound)

The chromene compound of the present invention is generally existent as an achromatic, light yellow or light green solid or viscous liquid at normal temperature and normal pressure and can be confirmed by the following means (a) to (c).

(a) When the proton nuclear magnetic resonance spectrum ($^1$H-NMR) of the chromene compound is measured, peaks based on an aromatic proton and an alkene proton appear at δ of around 5.0 to 9.0 ppm and peaks based on the protons of an alkyl group and an alkylene group appear at _67 of around 1.0 to 4.0 ppm. By comparing these spectral intensities relatively, the number of the protons of bonds can be known.

(b) The composition of a corresponding product can be determined by elemental analysis.

(c) When the $^{13}$C-nuclear magnetic resonance spectrum ($^{13}$C-NMR) of the chromene compound is measured, a peak based on the carbon of an aromatic hydrocarbon group appears at δ of around 110 to 160 ppm, peaks based on the carbons of an alkene and an alkyne appear at δ of around 80 to 140 ppm, and peaks based on the carbons of an alkyl group and an alkylene group appear at δ of around 20 to 80 ppm.

<Production of Chromene Compound>

The process for producing the chromene compound of the present invention is not particularly limited and may be any synthetic process.

The chromene compound represented by the above formula (1) can be advantageously produced by the following process.

That is, the chromene compound can be advantageously produced by reacting a naphthol compound represented by the following formula (6) with a propargyl alcohol compound represented by the following formula (7) in the presence of an acid catalyst.

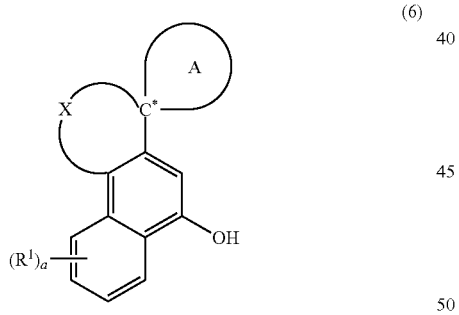

(6)

(In the above formula, R$^1$, X, A, C* and "a" are as defined in the above formula (1).)

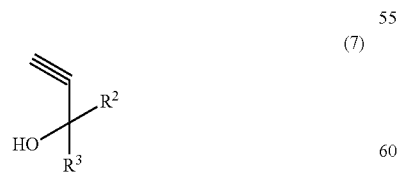

(7)

(In the above formula, R$^2$ and R$^3$ are as defined in the above formula (1).)

The reaction ratio of the naphthol compound to the propargyl alcohol compound is selected from a wide range, preferably a range from 1:10 to 10:1 (molar ratio).

Examples of the acid catalyst include sulfuric acid, benzenesulfonic acid, p-toluenesulfonic acid, camphorsulfonic acid, methanesulfonic acid, pyridium salts of p-toluenesulfonic acid, silica gel and acid alumina. The acid catalyst is preferably used in an amount of 0.1 to 10 parts by weight based on 100 parts by weight of the total of the naphthol compound and the propargyl alcohol compound. The reaction temperature is preferably 0 to 200° C. An aprotic organic solvent such as N-methylpyrrolidone, dimethyl formamide, tetrahydrofuran, benzene or toluene is preferably used as the solvent. The method of purifying the product obtained through the above reaction is not particularly limited. For example, the obtained product may be purified by carrying out silica gel column purification and further recrystallization.

A description is subsequently given of the naphthol compound and the propargyl alcohol compound.

(Naphthol Compound and Synthesis Method Thereof)

The naphthol compound of the present invention can be synthesized in accordance with reaction methods described in, for example, research papers such as Journal of Organic Chemistry 69(10)3282-3293, 2004, Synthetic Communications 23(16)2241-2249 (1993) and WO01/60881.

The following method is preferably employed to synthesize a naphthol compound represented by the following formula (8).

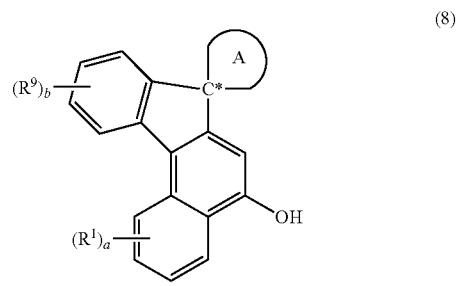

(8)

In the above formula, R$^1$, A, C* and "a" are as defined in the above formula (1), and R$^9$ and "b" are as defined in the above formula (5).

A benzophenone compound represented by the following formula (9) as a starting material is subjected to a Stobbe reaction, a cyclization reaction and a hydrolysis reaction so as to obtain a carboxylic acid compound represented by the following formula (10).

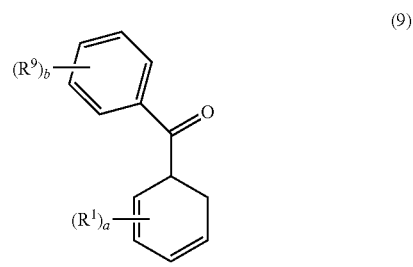

(9)

(In the above formula, R$^1$, R$^9$, "a" and "b" are as defined in the above formula (8).)

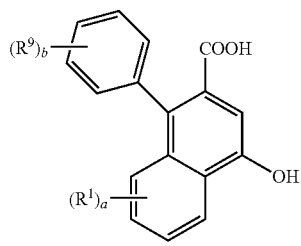

(10)

Thereafter, this carboxylic acid represented by the formula (10) is benzylated by using a base such as potassium carbonate and benzyl chloride and then hydrolyzed to obtain a benzyl-protected carboxylic acid represented by the following formula (11).

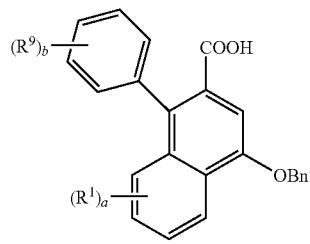

(11)

(In the above formula, Bn is a benzy group. The same shall apply hereinafter.)

Then, this benzyl-protected carboxylic acid represented by the above formula (11) is converted into an amine by a method such as Curtius rearrangement, Hofmann rearrangement or Lossen rearrangement, and a diazonium salt is prepared from the amine. This diazonium salt is converted into a bromide or iodide through a Sandmeyer reaction or the like to obtain a halide compound represented by the following formula (12).

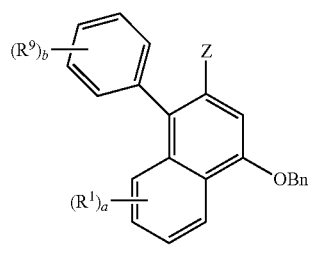

(12)

—Z= —Br or —I (In the above formula, "Z" is Br or I.)

Meanwhile, a cyclic ketone compound represented by the following formula (13) is prepared.

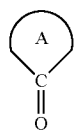

(13)

(In the above formula, "A" is as defined in the above formula (1).)

A cyclic ketone compound available on the market may be directly used as the cyclic ketone compound but may be synthesized by a known method. For example, methods described in documents such as Journal of Organic Chemistry 54(4)782-789, 1989 and Journal of Organic Chemistry 45(24)4876-4891, 1980 may be employed.

The halide compound of the above formula (12) is reacted with magnesium or lithium to prepare an organic metal reagent which is then reacted with the cyclic ketone compound of the above formula (13) at −80 to 70° C. in an organic solvent for 10 minutes to 4 hours to obtain an alcohol compound represented by the following formula (14).

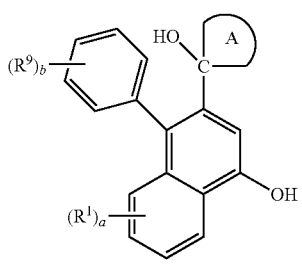

(14)

Thereafter, the alcohol compound represented by the above formula (14) is reacted under a neutral to acid condition at 10 to 120° C. for 10 minutes to 4 hours to carry out the spironization reaction and debenzylation reaction of the alcohol compound at the same time so as to synthesize the naphthol compound of the above formula (8) of interest. In this reaction, the reaction ratio of the above organic metal reagent to the cyclic ketone compound represented by the above formula (13) is selected from a wide range, preferably a range from 1:10 to 10:1 (molar ratio). The reaction temperature is preferably −80 to 70° C. An aprotic organic solvent such as diethyl ether, tetrahydrofuran, benzene or toluene is preferably used as the solvent. The spironization of the alcohol under a neutral to acid condition is preferably carried out by using an acid catalyst such as sulfuric acid, benzenesulfonic acid, p-toluenesulfonic acid or methanesulfonic acid. The acid catalyst is preferably used in an amount of 0.1 to 10 parts by weight based on 100 parts by weight of the alcohol. For this spironization, a solvent such as benzene, toluene or xylene is used.

(Preferred Naphthol Compounds)

Preferred examples of the naphthol compound are compounds represented by the following formulas.

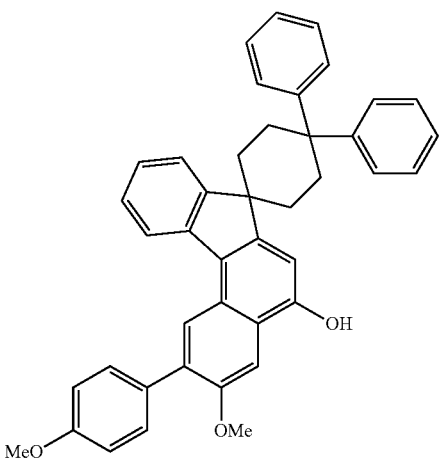

-continued

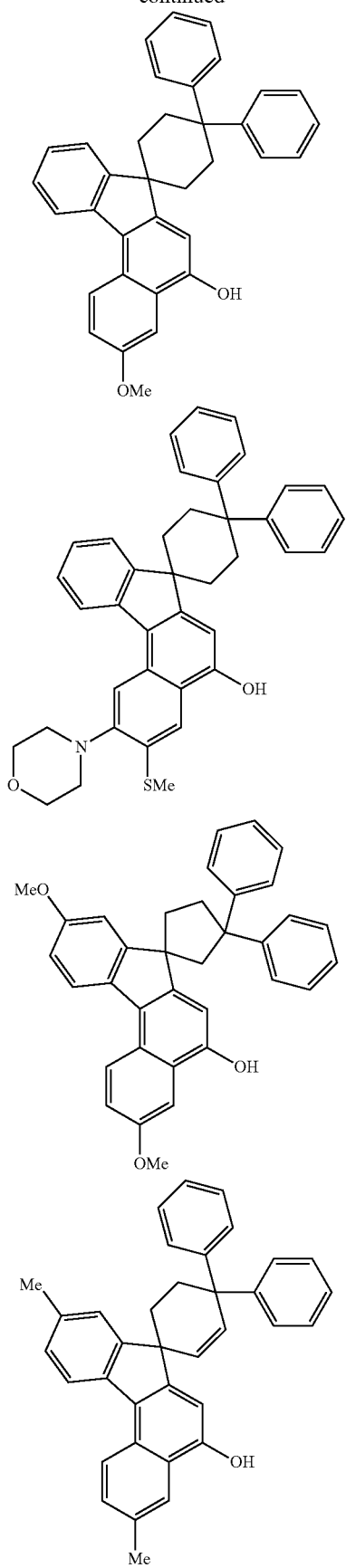

-continued

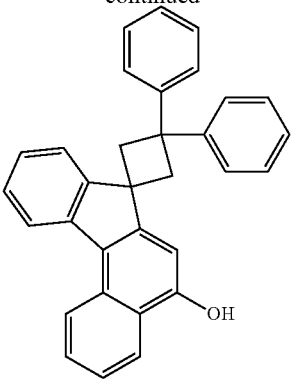

(Propargyl Alcohol Compound)

The propargyl alcohol compound represented by the above formula (7) can be synthesized by various methods. For example, it can be easily synthesized by reacting a ketone compound with a metal acetylene compound such as lithium acetylide.

The chromene compound of the present invention is obtained by reacting the above naphthol compound with the propargyl alcohol compound. The obtained chromene compound dissolves well in a general-purpose organic solvent such as toluene, chloroform or tetrahydrofuran. When the chromene compound represented by the above formula (1) is dissolved in such a solvent, the obtained solution is almost achromatic and transparent and exhibits an excellent photochromic function that it develops a color swiftly upon exposure to sunlight or ultraviolet light and reversibly returns to its original achromatic state swiftly by blocking the light.

(Uses and Purposes of Chromene Compound)

(Stabilizer to be Combined With)

Although the chromene compound of the present invention has high durability as it is, its durability can be further enhanced by using the following ultraviolet absorbent, optical stabilizer and antioxidant.

As the ultraviolet absorbent may be used known ultraviolet absorbents such as benzophenone-based compounds, benzotriazole-based compounds, cyanoacrylate-based compounds, triazine-based compounds and benzoate-based compounds. Cyanoacrylate-based compounds and benzophenone-based compounds are particularly preferred.

When the above ultraviolet absorbent is added to a photochromic curable composition which will be detailed hereinafter, it is preferably used in an amount of 0.001 to 5 parts by mass based on 100 parts by mass of the polymerizable monomer.

Known hindered amines may be used as the optical stabilizer, and known hindered phenols may be used as the antioxidant. When the above optical stabilizer and/or the above antioxidant is added to the photochromic curable composition which will be detailed hereinafter, the optical stabilizer and/or the antioxidant is preferably used in an amount of 0.01 to 10 parts by mass based on 100 parts by mass of the polymerizable monomer.

The chromene compound of the present invention exhibits excellent photochromic properties even in a polymer solid matrix. Therefore, the chromene compound of the present invention can be used for various purposes while it is dispersed in the polymer solid matrix. The polymer solid matrix is not particularly limited if the chromene compound of the present invention is uniformly dispersed therein, and examples of the optically preferred polymer solid matrix include thermoplastic resins such as methyl polyacrylate, ethyl polyacrylate, methyl polymethacrylate, ethyl polymethacrylate, polystyrene, polyacrylonitrile, polyvinyl alcohol, polyacrylamide, poly(2-hydroxyethyl methacrylate), polydimethylsiloxane and polycarbonate.

A thermosetting resin obtained by polymerizing a radically polymerizable polyfunctional monomer may also be used as the above polymer solid matrix. Examples of the radically polymerizable polyfunctional monomer include polyacrylate and polymethacrylate compounds such as ethylene glycol diacrylate, diethylene glycol dimethacrylate, triethylene glycol dimethacrylate, tetraethylene glycol dimethacrylate, ethylene glycol bisglycidyl methacrylate, bisphenol A dimethacrylate, 2,2-bis(4-methacryloyloxyethoxyphenyl)propane and 2,2-bis(3,5-dibromo-4-methacryloyloxyethoxyphenyl) propane; polyallyl compounds such as diallyl phthalate, diallyl terephthalate, diallyl isophthalate, diallyl tartarate, diallyl epoxysuccinate, diallyl fumarate, diallyl chlorendate, diallyl hexaphthalate, diallyl carbonate, allyl diglycol carbonate and trimethyloipropane triallyl carbonate; polythioacrylate and polythiomethacrylate compounds such as 1,2-bis(methacryloylthio)ethane, bis(2-acryloylthioethyl)ether and 1,4-bis(methacryloylthiomethyl)benzene; acrylate and methacrylate compounds such as glycidyl acrylate, glycidyl methacrylate, β-methylglycidyl methacrylate, bisphenol A-monoglycidyl ether-methacrylate, 4-glycidyloxy methacrylate, 3-(glycidyl-2-oxyethoxy)-2-hydroxypropyl methacrylate, 3-(glycidyloxy-1-isopropyloxy)-2-hydroxypropyl acrylate and 3-glycidyloxy-2-hydroxypropyloxy)-2-hydroxypropyl acrylate; and divinyl benzene.

Copolymers obtained by copolymerizing the above radically polymerizable polyfunctional monomers with radically polymerizable monofunctional monomers may also be used as the above polymer matrix. The radically polymerizable monofunctional monomers include unsaturated carboxylic acids such as acrylic acid, methacrylic acid and maleic anhydride; acrylate and methacrylate compounds such as methyl acrylate, methyl methacrylate, benzyl methacrylate, phenyl methacrylate and 2-hydroxyethyl methacrylate; fumarate compounds such as diethyl fumarate and diphenyl fumarate; thioacrylate and thiomethacrylate compounds such as methyl thioacrylate, benzyl thioacrylate and benzyl thiomethacrylate; and vinyl compounds such as styrene, chlorostyrene, methylstyrene, vinyl naphthalene, α-methylstyrene dimer and bromostyrene.

As the method of dispersing the chromene compound of the present invention into the above polymer solid matrix, methods known per se may be employed. The methods include one in which the above thermoplastic resin and the chromene compound are kneaded together while they are molten to disperse the chromene compound into the resin, one in which the chromene compound is dissolved in the above polymerizable monomer and then a polymerization catalyst is added to polymerize the polymerizable monomer by heat or light so as to disperse the chromene compound into the resin, and one in which the surface of the above thermoplastic resin or the above thermosetting resin is dyed with the chromene compound to disperse the chromene compound into the resin.

The chromene compound of the present invention can be widely used as a photochromic material for use as, for example, recording materials such as recording materials substituting silver halide photosensitive materials, copy materials, printing photosensitive materials, recording materials for cathode ray tubes, photosensitive materials for lasers and photosensitive materials for holography. A photochromic material comprising the chromene compound of the present invention may also be used as a photochromic lens material, optical filter material, display material or material for actinometers and ornaments.

The process for manufacturing, a photochromic lens by using the chromene compound of the present invention as a photochromic lens material is not particularly limited if uniform light control performance is obtained. Examples of the process include one in which a polymer film containing the chromene compound of the present invention uniformly dispersed therein is sandwiched between lenses, one in which the chromene compound of the present invention is dispersed into the above polymerizable monomer and the polymerizable monomer is polymerized by a predetermined technique, one in which the chromene compound of the present invention is dissolved in, for example, silicone oil, the resulting solution is impregnated into the surface of a lens at 150 to 200° C. over 10 to 60 minutes, and the surface is further coated with a curable substance to obtain a photochromic lens, and one in which the above polymer film is formed on the surface of a lens and the surface is coated with a curable substance to obtain a photochromic lens.

To manufacture a photochromic lens by using a photochromic curable composition comprising the chromene compound of the present invention and a polymerizable monomer, the curable composition may also be used as a coating agent. Stated more specifically, this coating agent is applied to the surface of a lens substrate and cured to manufacture a photochromic lens. At this point, the lens substrate may be subjected to a surface treatment with an alkaline solution or a plasma treatment in advance. A primer may be further applied so as to improve adhesion between the substrate and the coating film by carrying out or not carrying out the above surface treatment.

EXAMPLES

The following examples are provided for the purpose of further illustrating the present invention but are in no way to be taken as limiting.

Example 1

Synthesis of Chromene Compound E1

(Synthesis of Naphthol Compound)

50.0 g (172 mmol) of 3-bromo-4-methoxybenzophenone and 28.7 g (189 mmol) of 4-methoxyphenylboronic acid were added to 250 ml of 1,2-dimethoxyethane, and 25 ml of ethanol, 400 g of a 10% sodium carbonate aqueous solution and 0.05 g (0.043 mmol) of tetrakistriphenylphosphine palladium were added to the resulting solution to carry out a reaction at 78° C. After 3 hours, 1,000 ml of toluene was added to the reaction solution, an organic layer was washed with water to remove the solvent, and recrystallization was carried out with 200 ml of methanol to obtain 4-methoxy-3-(4-methoxyphenyl)benzophenone represented by the following formula as 51.6 g (162 mmol, yield of 94%) of a white solid.

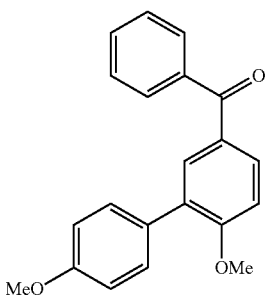 [SMILES: COc1ccc(-c2cc(C(=O)c3ccccc3)ccc2OC)cc1]

This benzophenone compound and 32.5 g (186 mmol) of diethyl succinate were dissolved in 150 ml of tetrahydrofuran. A tetrahydrofuran solution containing 23.6 g (211 mmol) of potassium-t-butoxide was added dropwise to this solution to carry out a reaction at 55° C. for 2 hours. Thereafter, the obtained reaction solution was washed with concentrated hydrochloric acid and a sodium chloride aqueous solution to remove the solvent. 82.7 g (810 mmol) of acetic anhydride, 13.3 g (162 mmol) of sodium acetate and 200 ml of toluene were added to the obtained orange oil to carry out a reaction at a reflux temperature for 2 hours. Thereafter, the reaction solution was washed with water to remove the solvent. 200 ml of methanol and 265 g of a 10% sodium hydroxide aqueous solution were added to the obtained red-brown oil to carry out a reaction at a reflux temperature for 3 hours. Thereafter, methanol was distilled off, 300 ml of concentrated hydrochloric acid and toluene was added, and an organic layer was washed with water to remove the solvent. 600 ml of ethyl acetate was added to the resulting product, stirred at a reflux temperature for 1 hour and cooled to 5° C. The precipitated solid was separated by filtration, the solvent of the filtrate was removed, 800 ml of toluene was added and stirred at a reflux temperature for 1 hour, and the obtained product was cooled to 5° C. The precipitated solid was filtered to obtain a carboxylic acid compound represented by the following formula as 17.7 g (44.1 mmol, yield of 27%) of a light yellow solid.

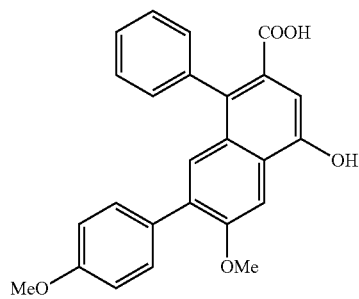 [SMILES: COc1ccc(-c2cc3c(-c4ccccc4)c(C(=O)O)cc(O)c3cc2OC)cc1]

This carboxylic acid compound was dissolved in 177 ml of dimethyl formamide, and 15.2 g (110 mmol) of potassium carbonate and 12.3 g (96.9 mmol) of benzyl chloride were added to the resulting solution to carry out a reaction at 60° C. for 2 hours. Thereafter, 500 ml of toluene was added, and an organic layer was washed with water to remove the solvent. 170 ml of 2-propanol and 110 g of a 20% sodium hydroxide aqueous solution were added to the resulting product to carry out a reaction at a reflux temperature for 4 hours. Thereafter, 2-propanol was removed, 200 ml of concentrated hydrochloride acid and tetrahydrofuran was added, and an organic layer was washed with a 10% sodium chloride aqueous solution to remove the solvent. 200 ml of toluene was added, stirred at a reflux temperature for 1 hour, cooled to 5° C. and stirred for 1 hour, and the precipitated solid was filtered to obtain a carboxylic acid material which was represented by the following formula and protected by benzyl as 19.0 g (38.8 mmol, yield of 88%) of a white solid.

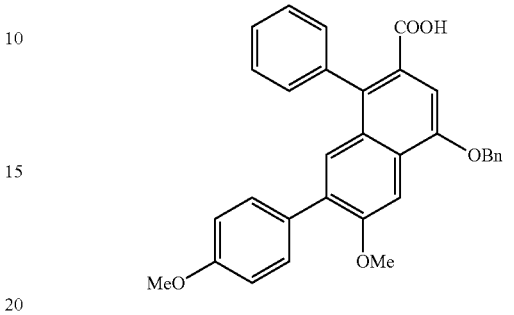

This product was dispersed into 190 ml of toluene, 11.7 g (116 mmol) of triethylamine and 13.8 g (50.3 mmol) of diphenylphosphoryl azide were added to the resulting dispersion and stirred at 20° C. for 3 hours, and 9.1 g (197 mmol) of ethanol was added to the resulting solution to carry out a reaction at 70° C. for 1 hour. 21.7 g (387 mmol) of potassium hydroxide was added to this solution and stirred at a reflux temperature for 3 hours, and then an organic layer was washed with a 20% sodium chloride aqueous solution. The solvent was removed, and 360 ml of acetonitrile and 118 g (194 mmol) of 6% hydrochloride acid were added and cooled to 5° C. 12.2 g (58.1 mmol) of a 33% sodium nitrite aqueous solution and 64.3 g (194 mmol) of a 50% potassium iodide aqueous solution were added dropwise to the obtained solution and stirred at 20° C. for 3 hours. After the reaction, toluene was added, an organic layer was washed with water and removed, and the resulting product was purified by chromatography using silica gel so as to obtain an iodine compound represented by the following formula as 15.6 g (27.3 mmol, yield of 70%) of a light yellow solid.

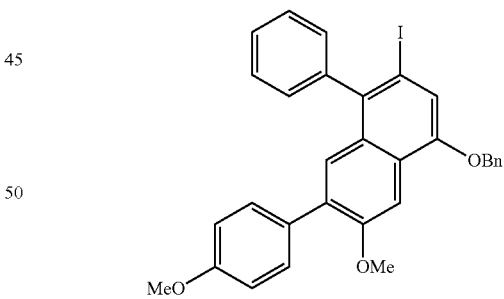

The ketone compound was synthesized as follows. First, 12.4 g (50 mmol) of 4,4-diphenyl-2-cyclohexen-1-one was dissolved in 124 ml of ethyl acetate, and 2.5 g of 5% palladium carbon (containing 50 wt % of water) was added to the resulting solution and stirred at 23° C. in a hydrogen atmosphere for 24 hours. Thereafter, the reaction solution was filtered to remove the solvent and purified by chromatography using silica gel to obtain 4,4-diphenylcycicohexanone as 11.5 g (29.0 mmol, yield of 92%) of a white solid.

5.73 g (10.0 mmol) of the iodine compound represented by the above formula was dissolved in 60 ml of toluene and cooled to −10° C. 6.9 ml (11.0 mmol) of n-butyl lithium (1.6 M hexane solution) was added dropwise to this solution, and 2.75 g (11.0 mmol) of 4,4-diphenylcyclohexanone was subsequently added and stirred for 30 minutes. After the reaction solution was washed with water to remove the solvent, recrystallization was carried out with acetonitrile to obtain an alcohol compound represented by the following formula as 4.95 g (7.1 mmol, yield of 71%) of a white solid.

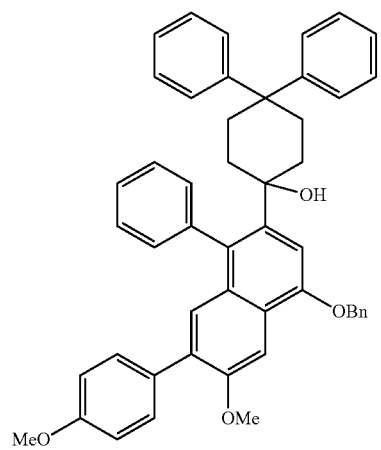 [SMILES: COc1ccc(-c2cc3c(-c4ccccc4)c(C4(O)CCC(c5ccccc5)(c5ccccc5)CC4)cc(OCc4ccccc4)c3cc2OC)cc1]

This alcohol compound was dissolved in 100 ml of toluene, and 5.02 g (26.4 mmol) of p-toluenesulfonic acid-hydrate was added to the resulting solution to carry out a reaction at a reflux temperature for 2 hours. The reaction solution was washed with water to remove the solvent and purified by chromatography using silica gel so as to obtain a naphthol compound represented by the following formula (naphthol compound No. 1) as 2.47 g (4.2 mmol, yield of 59%) of a light yellow solid.

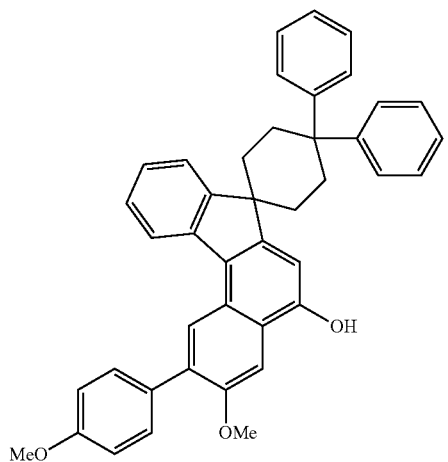

(15)

The elemental analysis values of this product were 85.61% of C and 6.29% of H which were almost equal to the calculated values of $C_{42}H_{36}O_3$ (C, 85.68%, H, 6.16%).

When the proton nuclear magnetic resonance spectrum of the product was measured, it showed 14H peaks based on an alkyl group and an alkylene group at δ of around 1.0 to 4.0 ppm and a 21H peak based on an aromatic proton at δ of around 5.0 to 9.0 ppm.

Further, when the $^{13}$C-nuclear magnetic resonance spectrum was measured, it showed a peak based on the carbon of an aromatic ring at δ of around 110 to 160 ppm and peaks based on the carbons of an alkyl group and an alkylene group at δ of around 20 to 80 ppm.

It was confirmed from the above results that the naphthol compound was a compound represented by the above formula (15).

(Synthesis of Chromene Compound)

1.18 g (2.0 mmol) of the above naphthol compound (15) and 0.81 g (3.0 mmol) of the following propargyl alcohol compound were dissolved in 50 ml of toluene, and 0.02 g of camphorsulfonic acid was added to the resulting solution and stirred under heating and reflux for 1 hour. After a reaction, the solvent was removed, and the obtained reaction product was purified by chromatography on silica gel to obtain 1.17 g of a white powder product. The yield was 70%.

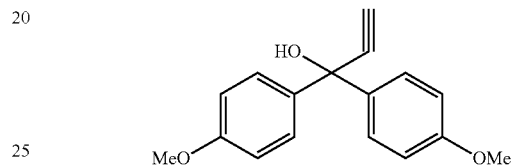

The elemental analysis values of this product were 84.59% of C and 5.93% of H which were almost equal to the calculated values of $C_{59}H_{50}O_5$ (C, 84.46%, H, 6.01%).

When the proton nuclear magnetic resonance spectrum of the product was measured, it showed 20H peaks based on a methyl proton and a methylene proton at δ of around 1.0 to 4.0 ppm and 30H peaks based on an aromatic proton and an alkene proton at δ of around 5.5 to 9.0 ppm.

Further, when the $^{13}$C-nuclear magnetic resonance spectrum was measured, it showed a peak based on the carbon of an aromatic ring at δ of around 110 to 160 ppm, a peak based on the carbon of an alkene at δ of around 80 to 140 ppm, and a peak based on the carbon of an alkyl at δ of around 20 to 60 ppm.

It was confirmed from the above results that the isolated product was a compound represented by the following formula (E1).

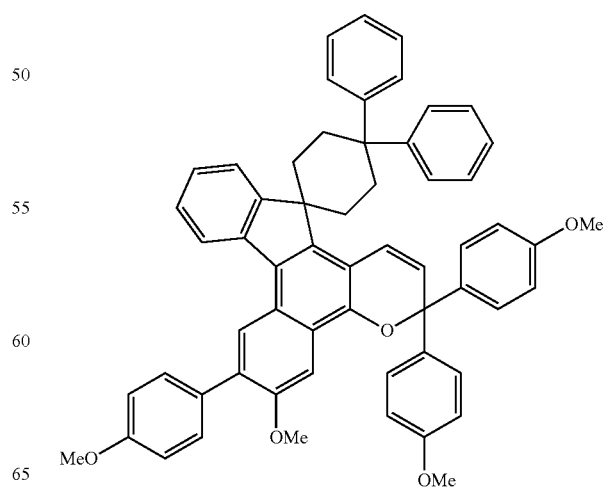

(E1)

Example 2

Evaluation of Photochromic Properties in Solution

The chromene compound (E1) obtained in Example 1 was dissolved in tetrahydrofuran to a concentration of 0.5 mM. This solution was fed to a quartz cell having an optical path length of 1 mm as a sample. The temperature of the sample was set to 23° C.±1° C., the UV-LED illuminator of Omron Corporation (ZUV-C20H controller, ZUV-H20MB head unit, ZUV-L18H lens unit) was used as a light source, and the distance between the sample and the light source was set to 50 mm so as to measure photochromic properties by developing a color by applying ultraviolet light having a wavelength of 365 nm. The photochromic properties were evaluated based on the following items.

[1] Maximum absorption wavelength (λmax): This is the maximum absorption wavelength after color development obtained by means of the spectrophotometer (MCPD2000M instantaneous multi-channel photodetector) of Otsuka Electronics Co., Ltd. and used as an index of color at the time of color development.

[2] Color optical density (ABS): This is absorbance after 0.5 second of exposure at the above maximum absorption wavelength and used as an index of color optical density. It can be said that as this value becomes larger, coloration by exposure becomes more marked and photochromic properties become better.

[3] Fading half period [T1/2]: This is a time required for the reduction of the absorbance at the above maximum absorption wavelength of the sample to a half value when exposure is stopped and used as an index of fading speed. As this time becomes shorter, the fading speed becomes higher.

As a result, as the photochromic properties of a tetrahydrofuran solution of the chromene compound (E1), the maximum absorption wavelength (λmax) was 570 nm, the developed color was gray, the color optical density (ABS) was 0.30, and the fading speed (T1/2) was 0.07 second.

Comparative Example 1

A chromene compound represented by the following formula (CE1) was synthesized in the same manner as in Example 1 except that 3,3,5,5-tetramethylcyclohexanone was used as a ketone compound.

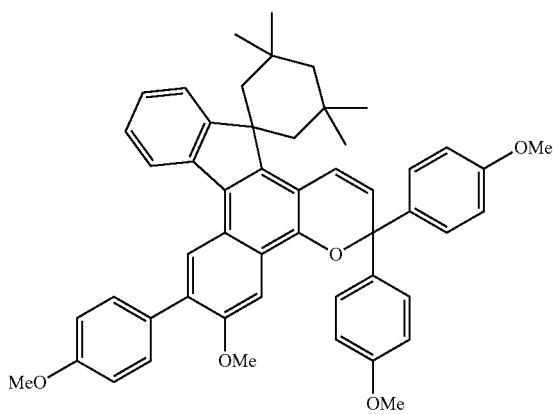

(CE 1)

The photochromic properties of this chromene compound (CE1) were evaluated in the same manner as in Example 2. The results are shown in Table 1.

TABLE 1

|  | Compound No. | Developed color | Maximum absorption wavelength λmax (nm) | Optical color density ABS | Fading half period T½ (sec) |
| --- | --- | --- | --- | --- | --- |
| Ex. 2 | E1 | Gray | 550 | 0.30 | 0.07 |
| C. Ex. 1 | CE1 | Gray | 550 | 0.78 | 27 |

Ex.: Example,
C. Ex.: Comparative Example

FIG. 1 shows time changes in the optical color density of each of the chromene compound (E1) of Example 2 and the chromene compound (CE1) of Comparative Example 1.

The fading half period of Example 2 in which the chromene compound of the present invention was used is much shorter than that of Comparative Example 1 (chromene compound of the above formula (CE1)), and the chromene compound of the present invention has photochromic properties that its color disappears instantaneously when exposure is stopped.

Example 3

Evaluation of Photochromic Cured Product

A photochromic cured product (photochromic optical article) manufactured by an in-mass technology was evaluated as follows. That is, 0.04 part by mass of the chromene compound obtained in Example 2, 13 parts by mass of tetraethylene glycol dimethacrylate (trade name, NK Ester 4G of Shin-Nakamura Chemical Co., Ltd.), 48 parts by mass of 2,2-bis[4-(methacryloxyethoxy)phenyl]propane (trade name, NK Ester BPE-100 of Shin-Nakamura Chemical Co., Ltd.), 2 parts by mass of polyethylene glycol monoallyl ether (trade name, Uniox PKA-5009 of NOF Corporation, molecular weight of 550), 20 parts by mass of trimethylolpropane trimethacrylate (trade name, NK Ester TMPT of Shin-Nakamura Chemical Co., Ltd.), 9 parts by mass of glycidyl methacrylate, 6 parts by mass of alpha-methylstyrene, 2 parts by mass of alpha-methylstyrene dimer and 1 part by mass of t-butylperoxy-2-ethyl hexanate as a polymerization initiator were fully mixed together to prepare a photochromic curable composition. Then, the obtained photochromic curable composition was cast into a mold composed of a glass sheet and a gasket made of an ethylene-vinyl acetate copolymer to carry out cast polymerization. Polymerization was carried out by using an air furnace, gradually raising the temperature from 30° C. to 90° C. over 18 hours and maintaining the temperature at 90° C. for 2 hours. After the end of polymerization, the obtained polymer was removed from the cast glass mold. The photochromic properties of the obtained polymer (thickness of 2 mm, photochromic cured product (optical article)) as a sample were evaluated in the same manner as in Example 2 except that the exposure time was changed to 1 second. Further, the fading half period of the sample at a temperature of 10° C. was evaluated. The results are shown in Table 2.

Comparative Example 2

A photochromic cured product was manufactured in the same manner as in Example 3 by using the chromene compound (CE1) used in Comparative Example 1 to evaluate its photochromic properties. Further, the fading half period at a sample temperature of 10° C. was evaluated. The results are shown in Table 2.

TABLE 2

| Compound No. | Developed color | Maximum absorption wavelength λmax (nm) | Otical color density ABS | Fading half period (23° C.) T½ (sec) | Fading half period (10° C.) T½ (sec) |
|---|---|---|---|---|---|
| Ex. 3 | E1 | Gray | 570 | 0.26 | 0.16 | 0.38 |
| C. Ex. 2 | CE1 | Gray | 570 | 0.91 | 61 | 385 |

Ex.: Example, C. Ex.: Comparative Example

The fading half period of Example 3 of the photochromic cured product (optical article) manufactured by using the chromene compound of the present invention is much shorter than that of Comparative Example 2 (chromene compound represented by the above formula (CE1)), and the photochromic cured product has photochromic properties that its color disappears instantaneously when exposure is stopped like when the chromene compound is in a solution form. Since the chromene compound of the present invention has a short fading half period even at a low temperature and can maintain instantaneous optical response, it can be used for various purposes.

Examples 4 to 15

Synthesis of Naphthol Compounds

Naphthol compounds were synthesized by synthesizing a halide compound (iodine compound) from a benzophenone compound as a starting material and reacting it with a ketone compound in accordance with the synthesis method described in Example 1. When the structures of the obtained products were analyzed by using the same structure confirming means as in Example 1, it was confirmed that they were naphthol compounds having structures shown in Tables 3 to 6. Table 7 shows the elemental analysis values, calculated values obtained from the structural formulas and characteristic $^1$H-NMR spectra of these compounds.

TABLE 3

| Example No. | Raw materials | | Naphthol compound No. | Naphthol compound |
|---|---|---|---|---|
| | Benzophenone compound | Ketone compound | | |
| 4 | [structure] | [structure] | 2 | [structure] |
| 5 | [structure] | [structure] | 3 | [structure] |

TABLE 3-continued

| Example No. | Raw materials | | Naphthol compound No. | Naphthol compound |
| --- | --- | --- | --- | --- |
| | Benzophenone compound | Ketone compound | | |
| 6 | (benzophenone with SMe and morpholino substituents) | 4,4-diphenylcyclohexanone | 4 | (naphthol product) |

TABLE 4

| Example No. | Raw materials | | Naphthol compound No. | Naphthol compound |
| --- | --- | --- | --- | --- |
| | Benzophenone compound | Ketone compound | | |
| 7 | 4-MeO, 4'-Me benzophenone | 4,4-diphenylcyclohex-2-enone | 5 | (naphthol product) |
| 8 | 4,4'-di-OMe benzophenone | 3,3-diphenylcyclopentanone | 6 | (naphthol product) |

TABLE 4-continued

| Example No. | Raw materials Benzophenone compound | Ketone compound | Naphthol compound No. | Naphthol compound |
|---|---|---|---|---|
| 9 | (benzophenone) | (3,3-diphenylcyclobutanone) | 7 | (spiro naphthol-cyclobutane with two phenyls) |

TABLE 5

| Example No. | Raw materials Benzophenone compound | Ketone compound | Naphthol compound No. | Naphthol compound |
|---|---|---|---|---|
| 10 | (benzophenone) | (4,4-dicyclohexylcyclohexanone) | 8 | (spiro naphthol-cyclohexane with two cyclohexyls) |
| 11 | (benzophenone with OMe and SMe substituents) | (4,4-dicyclohexylcyclohex-2-enone) | 9 | (spiro naphthol-cyclohexene with two cyclohexyls, MeO and SMe substituents) |

TABLE 5-continued

| Example No. | Raw materials | | Naphthol compound No. | Naphthol compound |
| --- | --- | --- | --- | --- |
| | Benzophenone compound | Ketone compound | | |
| 12 | (benzophenone) | (4,4-diisobutylcyclohexanone) | 10 | (spiro naphthol with 4,4-diisobutylcyclohexane) |

TABLE 6

| Example No. | Raw materials | | Naphthol compound No. | Naphthol compound |
| --- | --- | --- | --- | --- |
| | Benzophenone compound | Ketone compound | | |
| 13 | (benzoyl-benzodioxathiole with diisopropyl) | (4,4-diphenylcyclohexanone) | 11 | (spiro naphthol product) |
| 14 | (4-methoxybenzophenone) | (4,4-dibenzylcyclohexanone) | 12 | (spiro naphthol with OMe) |

TABLE 6-continued

| Ex-ample No. | Raw materials | | Naphthol compound No. | Naphthol compound |
|---|---|---|---|---|
| | Benzophenone compound | Ketone compound | | |
| 15 | (benzophenone) | (4,4-di-tert-butylcyclohexanone) | 13 | (spiro naphthol structure) |

TABLE 7

| Ex. No. | Elemental analytical values | | | | Calculated values | | | | $^1$H-NMR (ppm) |
|---|---|---|---|---|---|---|---|---|---|
| | C | H | N | S | C | H | N | S | |
| 4 | 86.89 | 6.45 | | | 87.10 | 6.27 | | | δ5.0-9.0 18H |
| | | | | | | | | | δ1.0-4.0 11H |
| 5 | 90.32 | 6.34 | | | 90.23 | 6.24 | | | δ5.0-9.0 19H |
| | | | | | | | | | δ1.0-4.0 8H |
| 6 | 80.35 | 6.53 | 2.31 | 5.42 | 80.24 | 6.39 | 2.40 | 5.49 | δ5.0-9.0 17H |
| | | | | | | | | | δ1.0-4.0 19H |
| 7 | 90.29 | 6.43 | | | 90.34 | 6.32 | | | δ5.0-9.0 19H |
| | | | | | | | | | δ1.0-4.0 10H |
| 8 | 84.39 | 6.13 | | | 84.31 | 6.06 | | | δ5.0-9.0 17H |
| | | | | | | | | | δ1.0-4.0 12H |
| 9 | 90.43 | 5.62 | | | 90.53 | 5.70 | | | δ5.0-9.0 19H |
| | | | | | | | | | δ1.0-4.0 4H |
| 10 | 86.89 | 6.45 | | | 87.10 | 6.27 | | | δ5.0-9.0 19H |
| | | | | | | | | | δ1.0-4.0 8H |
| 11 | 90.32 | 6.34 | | | 90.23 | 6.24 | | | δ5.0-9.0 17H |
| | | | | | | | | | δ1.0-4.0 19H |
| 12 | 80.35 | 6.53 | 2.31 | 5.42 | 80.24 | 6.39 | 2.40 | 5.49 | δ5.0-9.0 19H |
| | | | | | | | | | δ1.0-4.0 10H |
| 13 | 90.29 | 6.43 | | | 90.34 | 6.32 | | | δ5.0-9.0 17H |
| | | | | | | | | | δ1.0-4.0 19H |
| 14 | 84.39 | 6.13 | | | 84.31 | 6.06 | | | δ5.0-9.0 19H |
| | | | | | | | | | δ1.0-4.0 10H |
| 15 | 90.43 | 5.62 | | | 90.53 | 5.70 | | | δ5.0-9.0 19H |
| | | | | | | | | | δ1.0-4.0 4H |

Examples 16 to 38

Synthesis of Chromene Compounds

The naphthol compounds obtained in Example 1 and Examples 4 to 15 were reacted with propargyl alcohol by the same operation as in Example 1 to synthesize chromene compounds shown in Tables 8 to 13. When the structures of the obtained products were analyzed by using the same structure confirming means as in Example 1, it was confirmed that they were compounds represented by the structural formulas shown in Tables 8 to 13. Table 14 shows the elemental analysis values, calculated values obtained from the structural formulas and characteristic $^1$H-NMR spectra of these compounds.

TABLE 8

| Ex. No. | Co. No. | Naphthol compound No. | Propargyl alcohol compound | Chromene compound | Yield (%) |
|---|---|---|---|---|---|
| 16 | E2 | 1 | | | 38 |
| 17 | E3 | 2 | | | 62 |
| 18 | E4 | 2 | | | 67 |

TABLE 8-continued
| Ex. No. | Co. No. | Naphthol compound No. | Propargyl alcohol compound | Chromene compound | Yield (%) |
|---|---|---|---|---|---|
| 19 | E5 | 3 | 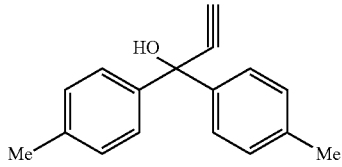 [SMILES: C#CC(O)(c1ccc(C)cc1)c1ccc(C)cc1] | 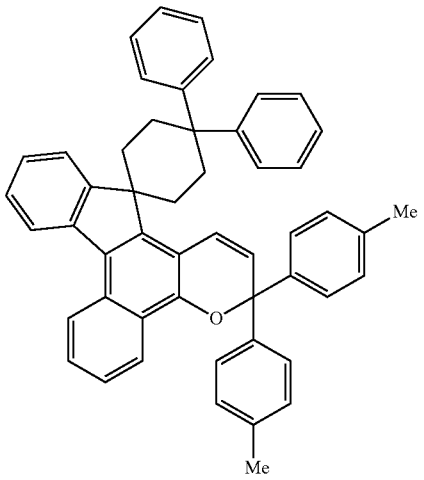 [SMILES: Cc1ccc(C2(c3ccc(C)cc3)C=Cc3c4c(c5ccccc5c3O2)-c2ccccc2C42CCC(c3ccccc3)(c3ccccc3)CC2)cc1] | 45 |
Ex.: Example,
Co.: Compound
TABLE 9
| Ex. No. | Co. No. | Naphthol compound No. | Propargyl alcohol compound | Chromene compound | Yield (%) |
|---|---|---|---|---|---|
| 20 | E6 | 3 | 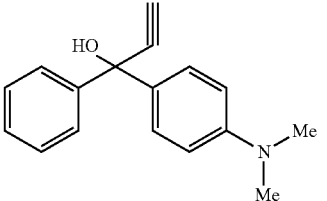 [SMILES: C#CC(O)(c1ccccc1)c1ccc(N(C)C)cc1] | 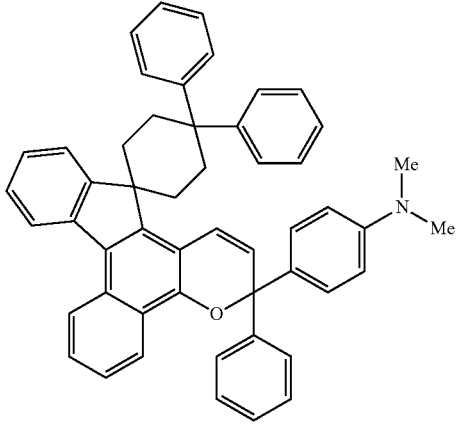 [SMILES: CN(C)c1ccc(C2(c3ccccc3)C=Cc3c4c(c5ccccc5c3O2)-c2ccccc2C42CCC(c3ccccc3)(c3ccccc3)CC2)cc1] | 63 |

TABLE 9-continued

| Ex. No. | Co. No. | Naphthol compound No. | Propargyl alcohol compound | Chromene compound | Yield (%) |
|---|---|---|---|---|---|
| 21 | E7 | 4 | 1-(4-methoxyphenyl)-1-phenyl-2-propyn-1-ol | (chromene structure with morpholino, SMe, OMe, and diphenyl spiro groups) | 41 |
| 22 | E8 | 4 | 1,1-bis(4-methoxyphenyl)-2-propyn-1-ol | (chromene structure with morpholino, SMe, two OMe, and diphenyl spiro groups) | 52 |
| 23 | E9 | 5 | 1,1-bis(4-butoxyphenyl)-2-propyn-1-ol | (chromene structure with two Me, two OBu, and diphenyl spiro groups) | 55 |

Ex.: Example,
Co.: Compound

TABLE 10

| Ex. No. | Co. No. | Raw materials Naphthol compound No. | Propargyl alcohol compound | Chromene compound | Yield (%) |
|---|---|---|---|---|---|
| 24 | E10 | 5 | | | 61 |
| 25 | E11 | 6 | | | 49 |
| 26 | E12 | 7 | | | 24 |

TABLE 10-continued

| | | Raw materials | | | |
|---|---|---|---|---|---|
| Ex. No. | Co. No. | Naphthol compound No. | Propargyl alcohol compound | Chromene compound | Yield (%) |
| 27 | E13 | 7 | (structure) | (structure) | 46 |

Ex.: Example,
Co.: Compound

TABLE 11

| | | Raw materials | | | |
|---|---|---|---|---|---|
| Ex. No. | Co. No. | Naphthol compound No. | Propargyl alcohol compound | Chromene compound | Yield (%) |
| 28 | E14 | 8 | (structure) | (structure) | 49 |

TABLE 11-continued

| Ex. No. | Co. No. | Raw materials Naphthol compound No. | Propargyl alcohol compound | Chromene compound | Yield (%) |
|---|---|---|---|---|---|
| 29 | E15 | 8 | | | 61 |
| 30 | E16 | 9 | | | 55 |
| 31 | E17 | 10 | | | 34 |

Ex.: Example,
Co.: Compound

TABLE 12

| Ex. No. | Co. No. | Raw materials Naphthol compound No. | Propargyl alcohol compound | Chromene compound | Yield (%) |
|---|---|---|---|---|---|
| 32 | E18 | 11 | 1-ethynyl-1,1-bis(4-methoxyphenyl)methanol | (chromene structure) | 68 |
| 33 | E19 | 11 | 1-ethynyl-1-phenyl-1-(4-morpholinophenyl)methanol | (chromene structure) | 71 |
| 34 | E20 | 12 | 1-ethynyl-1,1-bis(4-methoxyphenyl)methanol | (chromene structure) | 33 |

TABLE 12-continued

| Ex. No. | Co. No. | Naphthol compound No. | Propargyl alcohol compound | Chromene compound | Yield (%) |
|---|---|---|---|---|---|
| 35 | E21 | 13 | | | 42 |

Ex.: Example,

Co.: Compound

TABLE 13

| Ex. No. | Co. No. | Naphthol compound No. | Propargyl alcohol compound | Chromene compound | Yield (%) |
|---|---|---|---|---|---|
| 36 | E22 | 3 | | | 58 |

TABLE 13-continued

| Ex. No. | Co. No. | Naphthol compound No. | Propargyl alcohol compound | Chromene compound | Yield (%) |
|---|---|---|---|---|---|
| 37 | E23 | 3 | (HO, Me, vinyl, furan-2-yl) | spiro-fluorene-cyclohexane-diphenyl chromene with Me and furan-2-yl | 45 |
| 38 | E24 | 3 | (HO, 4-MeO-phenyl, vinyl, furan-2-yl) | spiro-fluorene-cyclohexane-diphenyl chromene with 4-OMe-phenyl and furan-2-yl | 67 |

Ex.: Example,
Co.: Compound

TABLE 14

| Example No. | Compound No. | Elemental analytical values | | | | Calculated values | | | | $^1$H-NMR (ppm) |
|---|---|---|---|---|---|---|---|---|---|---|
| | | C | H | N | S | C | H | N | S | |
| 16 | E2 | 86.23 | 5.95 | | | 86.11 | 5.98 | | | δ5.0-9.0 31H |
| | | | | | | | | | | δ1.0-4.0 17H |
| 17 | E3 | 85.20 | 5.94 | | | 85.22 | 6.05 | | | δ5.0-9.0 27H |
| | | | | | | | | | | δ1.0-4.0 17H |
| 18 | E4 | 84.04 | 6.20 | 1.72 | | 83.83 | 6.27 | 1.78 | | δ5.0-9.0 27H |
| | | | | | | | | | | δ1.0-4.0 22H |
| 19 | E5 | 91.24 | 6.34 | | | 91.31 | 6.31 | | | δ5.0-9.0 27H |
| | | | | | | | | | | δ1.0-4.0 17H |
| 20 | E6 | 89.49 | 6.25 | 1.98 | | 89.31 | 6.32 | 2.04 | | δ5.0-9.0 28H |
| | | | | | | | | | | δ1.0-4.0 17H |
| 21 | E7 | 82.29 | 6.06 | 1.79 | 4.02 | 82.16 | 6.14 | 1.74 | 3.99 | δ5.0-9.0 27H |
| | | | | | | | | | | δ1.0-4.0 22H |
| 22 | E8 | 80.46 | 6.23 | 1.73 | 3.95 | 80.64 | 6.16 | 1.68 | 3.84 | δ5.0-9.0 26H |
| | | | | | | | | | | δ1.0-4.0 25H |
| 23 | E9 | 87.02 | 7.02 | | | 87.15 | 6.94 | | | δ5.0-9.0 26H |
| | | | | | | | | | | δ1.0-4.0 32H |
| 24 | E10 | 85.58 | 6.46 | 1.74 | | 85.79 | 8.30 | 1.79 | | δ5.0-9.0 25H |
| | | | | | | | | | | δ1.0-4.0 25H |
| 25 | E11 | 83.57 | 5.87 | | | 83.40 | 5.92 | | | δ5.0-9.0 26H |
| | | | | | | | | | | δ1.0-4.0 18H |
| 26 | E12 | 91.75 | 5.58 | | | 91.82 | 5.57 | | | δ5.0-9.0 30H |
| | | | | | | | | | | δ1.0-4.0 4H |

TABLE 14-continued

| Example No. | Compound No. | Elemental analytical values C | H | N | S | Calculated values C | H | N | S | $^1$H-NMR (ppm) |
|---|---|---|---|---|---|---|---|---|---|---|
| 27 | E13 | 87.49 | 6.11 | 1.99 | | 87.30 | 6.01 | 2.04 | | δ5.0-9.0 28H |
| | | | | | | | | | | δ1.0-4.0 13H |
| 28 | E14 | 84.04 | 6.20 | 1.72 | | 83.83 | 6.27 | 1.78 | | δ5.0-9.0 27H |
| | | | | | | | | | | δ1.0-4.0 22H |
| 29 | E15 | 91.24 | 6.34 | | | 91.31 | 6.31 | | | δ5.0-9.0 27H |
| | | | | | | | | | | δ1.0-4.0 17H |
| 30 | E16 | 89.49 | 6.25 | 1.98 | | 89.31 | 6.32 | 2.04 | | δ5.0-9.0 28H |
| | | | | | | | | | | δ1.0-4.0 17H |
| 31 | E17 | 82.29 | 6.06 | 1.79 | 4.02 | 82.16 | 6.14 | 1.74 | 3.99 | δ5.0-9.0 27H |
| | | | | | | | | | | δ1.0-4.0 22H |
| 32 | E18 | 80.46 | 6.23 | 1.73 | 3.95 | 80.64 | 6.16 | 1.68 | 3.84 | δ5.0-9.0 26H |
| | | | | | | | | | | δ1.0-4.0 25H |
| 33 | E19 | 87.02 | 7.02 | | | 87.15 | 6.94 | | | δ5.0-9.0 26H |
| | | | | | | | | | | δ1.0-4.0 32H |
| 34 | E20 | 85.58 | 6.46 | 1.74 | | 85.79 | 6.30 | 1.79 | | δ5.0-9.0 26H |
| | | | | | | | | | | δ1.0-4.0 25H |
| 35 | E21 | 83.57 | 5.87 | | | 83.40 | 5.92 | | | δ5.0-9.0 26H |
| | | | | | | | | | | δ1.0-4.0 18H |
| 36 | E22 | 88.64 | 6.18 | | | 88.49 | 6.27 | | | δ5.0-9.0 27H |
| | | | | | | | | | | δ1.0-4.0 11H |
| 37 | E23 | 88.43 | 5.97 | | | 88.39 | 6.00 | | | δ5.0-9.0 23H |
| | | | | | | | | | | δ1.0-4.0 11H |
| 38 | E24 | 86.84 | 5.80 | | | 86.98 | 5.78 | | | δ5.0-9.0 27H |
| | | | | | | | | | | δ1.0-4.0 11H |

Example 39

Synthesis of Chromene Compound

A siloxane compound (MCR-C12 of Gelest Inc.) represented by the following formula (16) was tosylated by using tosyl chloride and then reacted with lithium bromide to obtain a bromo compound represented by the following formula (17).

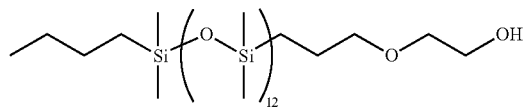

(16)

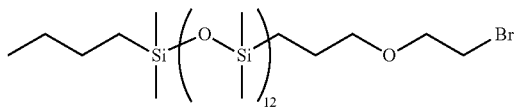

(17)

The bromo compound and 4-hydroxy-4'-methoxybenzophenone were subjected to a Williamson reaction under a basic condition to synthesize a benzophenone derivative represented by the following formula (18).

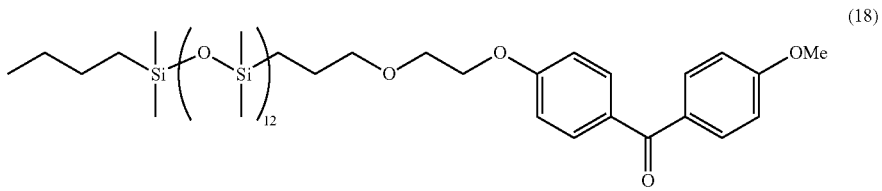

(18)

A propargyl alcohol compound represented by the following formula (19) was synthesized by reacting this benzophenone derivative with lithium acetylide.

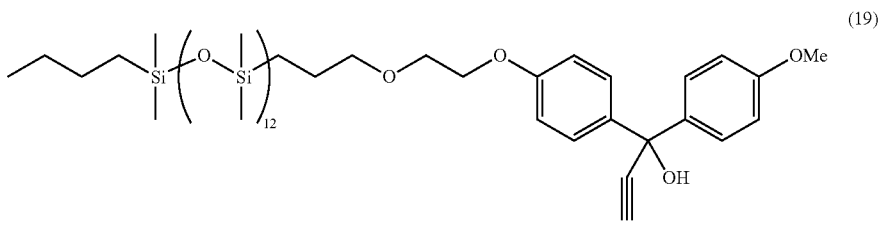

(19)

The propargyl alcohol compound represented by the above formula (19) and the naphthol compound (naphthol compound No. 3) obtained in Example 5 were used to carry out the same operation as in Example 1 so as to synthesize a chromene compound represented by the following formula (E25) (yield of 26%).

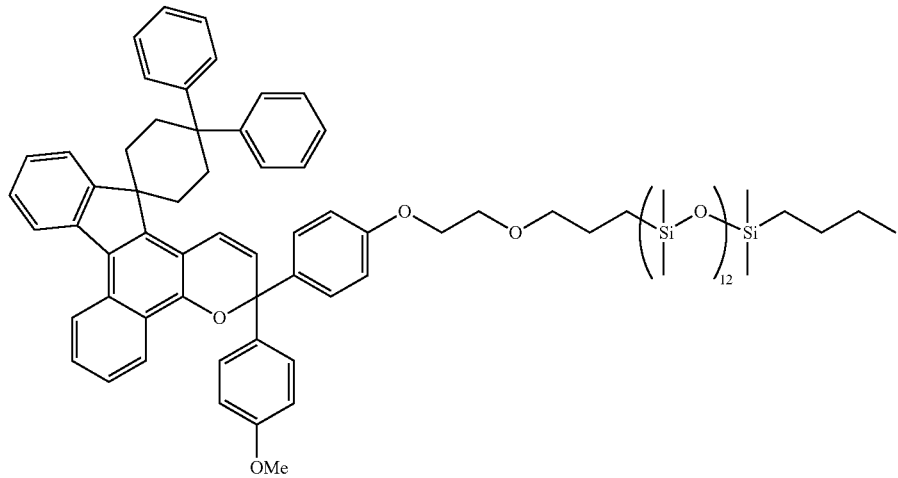

(E25)

The same structural confirming means as in Example 1 was used to analyze the structure of the obtained product.

Example 40

Synthesis of Chromene Compound

A benzophenone derivative was synthesized by hydrosilylating a mixture of a polydimethylsiloxane compound represented by the following formula (20), divinylbenzene and 4-methoxy-4'-vinylbenzophenone in the presence of chloroplatinic acid as a catalyst and further reacted with lithium acetylide to synthesize a propargyl alcohol compound represented by the following formula (21).

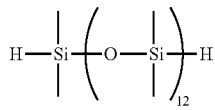

(20)

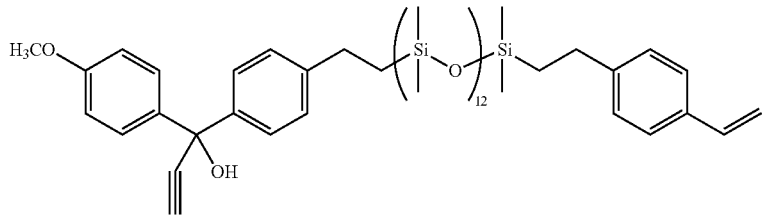

(21)

The propargyl alcohol compound represented by the above formula (21) and the naphthol compound obtained in Example 5 (naphthol compound No. 3) were used to carry out the same operation as in Example 1 so as to synthesize a chromene compound represented by the following formula (E26) (yield of 22%).

(E26)

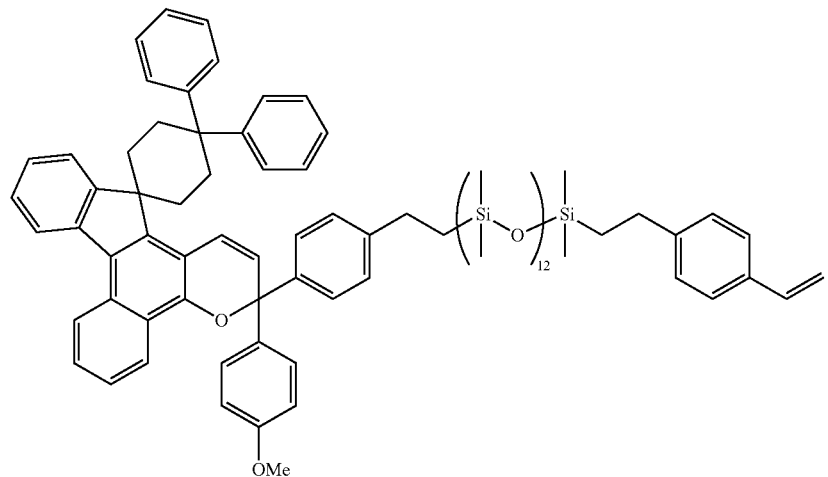

The same structural confirming means as in Example 1 was used to analyze the structure of the obtained product.

(Evaluation of Photochromic Properties)

Photochromic cured products were manufactured in the same manner as in Example 3 by using the chromene compounds obtained in Examples 16 to 40 to evaluate their photochromic properties. The results are shown in Table 15.

TABLE 15

| | Compound No. | Developed color | Maximum absorption wavelength λmax (nm) | Optical color density ABS | Fading half period (23° C.) T½ (sec) | Fading half period (10° C.) T½ (sec) |
|---|---|---|---|---|---|---|
| Ex. 16 | E2 | Green | 446 | 0.31 | 0.33 | 0.74 |
| Ex. 17 | E3 | Gray | 570 | 0.28 | 0.18 | 0.42 |
| Ex. 18 | E4 | Blue | 590 | 0.23 | 0.15 | 0.36 |
| Ex. 19 | E5 | Red purple | 554 | 0.29 | 0.25 | 0.55 |
| Ex. 20 | E6 | Blue | 580 | 0.21 | 0.09 | 0.26 |
| Ex. 21 | E7 | Yellow | 452 | 0.31 | 0.31 | 0.69 |
| Ex. 22 | E8 | Orange | 486 | 0.27 | 0.19 | 0.43 |
| Ex. 23 | E9 | Blue | 578 | 0.38 | 0.52 | 1.22 |
| Ex. 24 | E10 | Blue | 582 | 0.36 | 0.47 | 1.26 |
| Ex. 25 | E11 | Gray | 598 | 0.43 | 0.92 | 2.87 |
| Ex. 26 | E12 | Red | 538 | 0.41 | 1.16 | 3.75 |
| Ex. 27 | E13 | Blue | 590 | 0.25 | 0.27 | 0.64 |
| Ex. 28 | E14 | Purple | 566 | 0.25 | 0.16 | 0.41 |
| Ex. 29 | E15 | Gray | 578 | 0.22 | 0.15 | 0.38 |
| Ex. 30 | E16 | Blue green | 582 | 0.27 | 0.22 | 0.51 |
| Ex. 31 | E17 | Purple | 564 | 0.39 | 2.51 | 5.89 |
| Ex. 32 | E18 | Brown | 466 | 0.38 | 0.18 | 0.44 |
| Ex. 33 | E19 | Gray | 578 | 0.35 | 0.16 | 0.42 |
| Ex. 34 | E20 | Gray | 570 | 0.46 | 1.93 | 4.46 |
| Ex. 35 | E21 | Purple | 564 | 0.33 | 3.82 | 9.45 |
| Ex. 36 | E22 | Red | 546 | 0.22 | 0.22 | 0.52 |
| Ex. 37 | E23 | Purple | 560 | 0.19 | 0.18 | 0.49 |
| Ex. 38 | E24 | Blue | 572 | 0.31 | 0.39 | 1.09 |
| Ex. 39 | E25 | Purple | 562 | 0.22 | 0.12 | 0.24 |
| Ex. 40 | E26 | Purple | 568 | 0.21 | 0.11 | 0.28 |

Comparative Examples 3 to 5

Compounds represented by the following formulas (CE2) to (CE4) were synthesized as comparative examples.

(CE2)

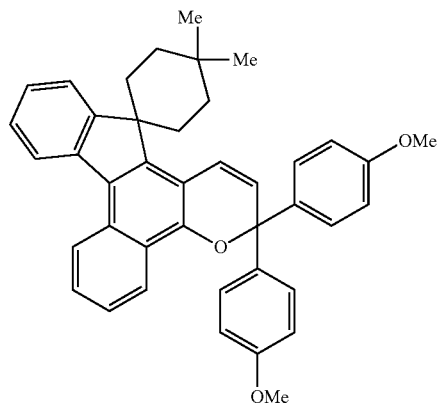

(CE3)

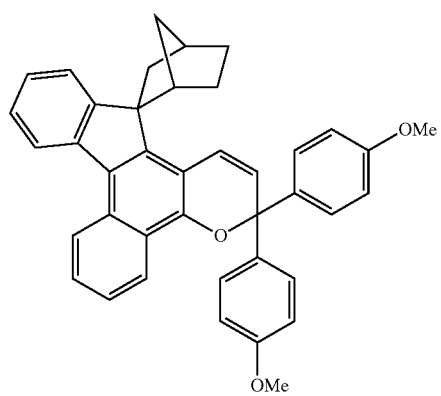

(CE4)

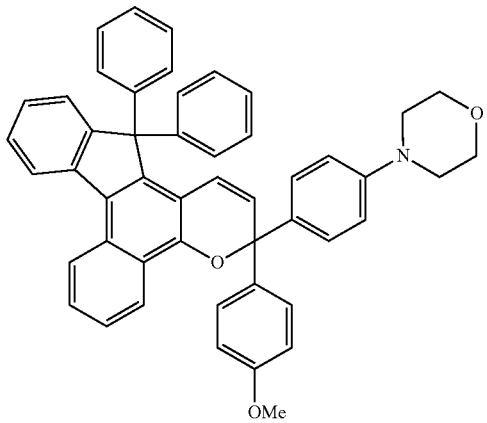

Photochromic cured products were manufactured in the same manner as in Example 3 by using these compounds to evaluate their photochromic properties. The results are shown in Table 16.

TABLE 16

| Compound No. | Developed color | Maximum absorption wavelength λmax (nm) | Optical color density ABS | Fading half period (23° C.) T½ (sec) | Fading half period (10° C.) T½ (sec) |
|---|---|---|---|---|---|
| C. Ex. 3 | CE2 | Purple | 568 | 1.24 | 220 | 1350 |
| C. Ex. 4 | CE3 | Purple | 564 | 0.86 | 52 | 342 |
| C. Ex. 5 | CE4 | Blue | 576 | 1.01 | 185 | 1100 |

C. Ex.: Comparative Example

It is understood that Examples 16 to 40 in which the chromene compound of the present invention was used have an extremely short fading half period like Example 3 and instantaneous optical response even at a low temperature. Meanwhile, although the chromene compounds used in Comparative Examples have a methyl group in the spiro ring (Comparative Example 3), a bicyclo ring as the spiro ring (Comparative Example 4) and a phenyl group but not a spiro structure (Comparative Example 5), all of the chromene compounds have a longer fading half period than that of the chromene compound of the present invention and very slow optical response especially at a low temperature.

Effect of the Invention

The chromene compound of the present invention has very quick optical response even when it is dispersed in a solution or a polymer solid matrix and a short fading half period even at a low temperature. In addition, it exhibits more excellent durability than other photochromic compounds.

Therefore, when a photochromic lens is manufactured by using the chromene compound of the present invention, it develops a color swiftly when it moves outside and fades to return to its original color swiftly when it returns inside from outside and further has such high durability that it can be used for a long time.

Since the chromene compound of the present invention exhibits the above excellent effect, it can be used for various purposes, for example, light control materials, hologram materials, ink materials, optical information devices, optical switch elements, photoresist materials and the like.

The invention claimed is:
1. A chromene compound represented by the following formula (5):

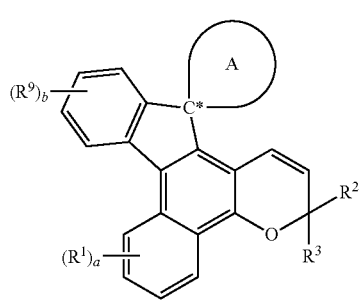

(5)

wherein $R^1$ is a hydroxyl group, alkyl group, haloalkyl group, cycloalkyl group, alkoxy group, amino group, heterocyclic group having a ring member nitrogen atom and bonded to a benzene ring to which the heterocyclic group is bonded via the nitrogen atom, cyano group, nitro group, formyl group, hydroxycarbonyl group, alkylcarbonyl group, alkoxycarbonyl group, halogen atom, aralkyl group, aralkoxy group, aryloxy group, aryl group, heteroaryl group, alkylthio group, cycloalkylthio group, arylthio group, heteroarylthio group or group having a siloxane bond, "a" is an integer of 0 to 4, provided that when "a" is 2 to 4, a plurality of $R^1$'s can be the same or different, or two $R^1$'s are bonded together to form a ring, $R^2$ and $R^3$ are each an alkyl group, aryl group, heteroaryl group, group represented by the following formula (2), or group represented by the following formula (3):

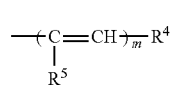

(2)

wherein $R^4$ is an aryl group or heteroaryl group, $R^5$ is a hydrogen atom, alkyl group or halogen atom, and "m" is an integer of 1 to 3,

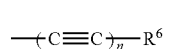

(3)

wherein $R^6$ is an aryl group or heteroaryl group, and "n" is an integer of 1 to 3, or $R^2$ and $R^3$ form an aliphatic ring together with carbon atoms to which $R^2$ and $R^3$ are bonded, C* is a Spiro carbon atom, a spiro ring A represented by the following formula is a saturated hydrocarbon ring or unsaturated hydrocarbon ring having 4 to 12 carbon atoms constituting the ring, and at least one ring member carbon atom constituting the Spiro ring A is a group represented by the following formula (4):

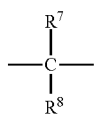 (4)

wherein R⁷ and R⁸ are each an alkyl group having 3 or more carbon atoms, aralkyl group, cycloalkyl group, aryl group or heteroaryl group, and R⁹ is a hydroxyl group, alkyl group, haloalkyl group, cycloalkyl group, alkoxy group, amino group, heterocyclic group having a ring member nitrogen atom and bonded to a benzene ring to which the heterocyclic group is bonded via the nitrogen atom, cyano group, nitro group, formyl group, hydroxycarbonyl group, alkylcarbonyl group, alkoxycarbonyl group, halogen atom, aralkyl group, aralkoxy group, aryloxy group, aryl group, heteroaryl group, alkylthio group, cycloalkylthio group, arylthio group, heteroarylthio group or group having a siloxane bond, "b" is an integer of 0 to 4, provided that when "b" is 2 to 4, a plurality of R⁹'s can be the same or different, or two R⁹'s are bonded together to form a ring.

2. The chromene compound according to claim 1, wherein the Spiro ring A is one member selected from the group consisting of the following formula:

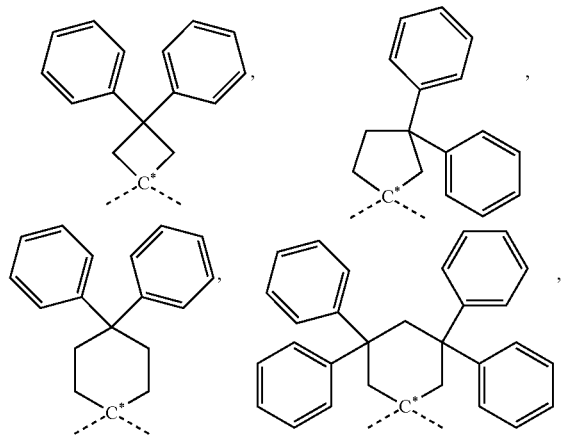

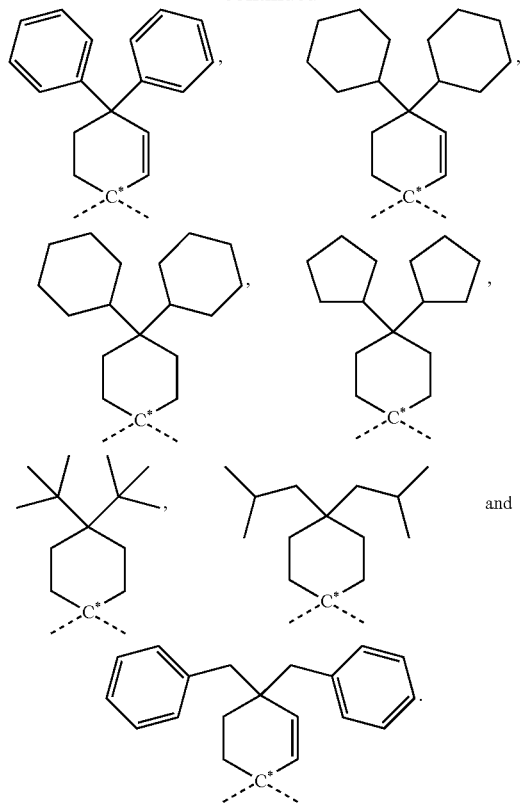 and

3. A photochromic curable composition comprising the chromene compound of claim 1 and a polymerizable monomer.

4. A photochromic optical article having a polymer molded product containing the chromene compound of claim 1 dispersed therein as a constituent member.

5. An optical article having an optical substrate all or part of at least one surface of which is coated with a polymer film comprising the chromene compound of claim 1 dispersed therein as a constituent member.

* * * * *